United States Patent [19]

Gong et al.

[11] Patent Number: 5,691,157
[45] Date of Patent: Nov. 25, 1997

[54] METHOD FOR DETECTING A MAMMAL'S PRIOR EXPOSURE TO RADIATION OR RADIOMIMETIC CHEMICALS

[75] Inventors: Joseph K. Gong, Williamsville; Chester A. Glomski, Buffalo, both of N.Y.

[73] Assignee: The Research Foundation of State University of New York, Amherst, N.Y.

[21] Appl. No.: 547,197

[22] Filed: Oct. 24, 1995

[51] Int. Cl.$^6$ .................................................. C01N 33/532
[52] U.S. Cl. ........................... 435/7.25; 435/2; 436/501; 436/542; 436/545; 436/546; 436/548; 436/56; 436/57; 436/63; 436/172; 436/805; 436/811; 530/388.22; 530/388.7; 424/93.73; 424/533
[58] Field of Search ..................... 435/7.25, 7.1, 435/2, 968; 436/501, 545, 546, 548, 542, 56, 57, 63, 172, 805, 811; 530/388.1, 388.15, 388.2, 388.22, 389.1, 388.7; 424/93.73, 533

[56] References Cited

U.S. PATENT DOCUMENTS

| | | | |
|---|---|---|---|
| 4,497,547 | 2/1985 | Allen et al. | 436/543 |
| 4,752,582 | 6/1988 | Vanderlaan et al. | |
| 4,752,583 | 6/1988 | Jensen et al. | |
| 4,767,710 | 8/1988 | Bigbee et al. | |
| 5,352,432 | 10/1994 | Meny et al. | 424/9 |

OTHER PUBLICATIONS

Gorbenko et al. "Influence of radiation of the . . ." 1995 Institute of Cryobiology and Cyomedicine Problems Ukranian Acad. Sci.
Biosis An 87:148473, Chifambar et al. "Inhibition of Hemoglobin . . ." 1987.
Embase An 94036696, Fujiwara et al. "Autoantibodies and . . ." 1994.
Biosis An 93:322048, Perera et al. "HPRT and Glycophorin A . . ." 1993.
Biosis An 96:158007, Mitsatis "Transgenic Models for detection . . ." 1995.
Gong et al., "A Method for Determining Residual Injury in the Hematopoietic System of the X-Irradiated Rat," *Radiation Research* 37(3):467–477 (1969).
Gong et al., "Effects of Low–Level (1.0 R) X–Irradiation on the Erythroid Response of the Rat Bone Marrow," *Radiation Research* 65:83–97 (1976).
Lawson et al., "Recurrent Decreases of Erythrocyte Electrophoretic Mobility in Rats Exposed to 1.0 R Whole–Body X–Radiation," *Cell Biophysics* 4:47–61 (1982).
Gong et al., "The Effects of Low Dose (Less than 1 Rad) X–Rays on the Erythropoietic Marrow," *Cell Biophysics* 5:143–162 (1983).
Langlois et al.,"Measurements of the Frequency of Human Erythrocytes with Gene Expression Loss Phenotypes at the Glycophorin A Locus," *Hum. Genet.* 74:353–362 (1986).
Langlois et al., "Evidence for Increased Somatic Cell Mutations at the Glycophorin A Locus in Atomic Bomb Survivors," *Science* 236:445–448 (1987).
Gong et al., "Iron Kinetics Effects of 88 Millirads: Partial--versus–Total Body X–Irradiation," *Cell Biophysics* 13:15–27 (1988).
Akiyama et al., "Evaluation of Four Somatic Mutation Assays as Biological Dosimeter in Humans," in *Radiation Research: A Twentieth–Century Perspective*, Dewey, et al., eds, vol. II Congress Proceedings, New York: Academic Press, pp. 77–182 (1992).
Jensen et al., "Biodosimetry of Ionizing Radiation in Humans Using Glycophorin A Genotoxicity Assay," *Radiation Research: A Twentieth–Century Perspective*, Dewey et al.,eds, vol. II Congress Proceedings, New York:Academic Press pp. 172–176 (1992).
Langlois et al., "Analysis of Somatic Cell Mutations at the Glycophorin A Locus in Atomic Bomb Survivors: A Comparative Study of Assay Methods," *Radiation Research* 136:111–117 (1993).

*Primary Examiner*—Paula K. Hutzell
*Assistant Examiner*—Rachel Heather Freed
*Attorney, Agent, or Firm*—Nixon, Hargrave, Devans & Doyle

[57] ABSTRACT

The present invention is directed to a method for detecting a mammal's prior exposure to radiation or radiomimetic agents. Labeled antibodies are employed to determine the quantity of transferrin receptors on the red blood cells of the mammal. The quantity of transferrin receptors on the red blood cells of the mammal is correlated to the mammal's prior exposure.

21 Claims, 7 Drawing Sheets

```
SEQ. ID. No. 1

1  ieftdiikql  sqntytprea  gsqkdenlay  yienlfhdfk  fskvwrdehy
 51  vkiqvknsvs  qnlvtinsgs  nidpveapeg  yvafskagev  tgklvhanfg
101  tkkdfeelny  svngslvivr  agkitfaekv  anaqsfnaig  vliymdrntf
151  pvveadlqff  ghahlgtgdp  ytpgfpsfnh  tqfppsqssg  lpsipvqtis
201  rapaeklfkn  megncppswn  idsscklels  qnqnvkltvn  nvlketriln 251  ifgvikgyee  pdryivvgaq  rdawgpgvak  ssvgtglllk  laqvfsdmis
301  kdgfrpsrsi  ifaswtagdy  gavgptewle  gylsslhlka  ftyinldkvv
351  lgtsnfkvsa  spllytlmgk  imqdvkhpid  gkylyrnsnw  iskieelsld
401  naafpflays  gipavsfcfc  ededypylgt  kldtyeiliq  kvpqlnqmvr
451  taaevaggfi  iklthdielt  ldyemynskl  lsfmkdlnqf  kadikdmgls 501  lqwlysargd  yfratsrltt  dfhnaektnr  fvmreindri  mkveyhflsp
551  yvsprespfr  hifwgsgsht  lsalvenlrl  rqknitafne  tlfrnqlala
601  twtiggvana  lsgdiwmidn  ef
```

*FIG. 1A*

```
SEQ. ID. NO. 2

1  mmdqarsafs  nlfggeplsy  trfslarqvd  gdnshvemkl  avdeeenadn
 51  ntkanvtkpk  rcsgsicygt  iavivfflig  fmigylgyck  gvepktecer
101  lagtespvre  epgedfpaar  rlywddlkrk  lseklbstdf  tstiklinen
151  syvpreagsq  kdenlalyve  nqfrefklsk  vwrdqhfvki  qvkdsaqnsv
201  iivdkngrlv  ylvenpggyv  ayskaatvtg  klvhanfgtk  kdfedlytpv
251  ngsivivrag  kitfaekvan  aeslnaigvl  iymdqtkfpi  vnaelsffgh
301  ahlgtgdpyt  pgfpsfnhtq  fppsrssglp  nipvqtisra  aaeklfgnme
351  gdcpsdwktd  stcrmvtses  knvkltvsnv  lkeikilnif  gvikgfvepd
401  hyvvvgaqrd  awgpgaaksg  vgtalilkla  qmfsdmvlkd  gfqpsrsiif
451  aswsagdfgs  vgatewlegy  lsslhlkaft  yinldkavlg  tsnfkvsasp
501  llytliektm  qnvkhpvtgq  flyqdsnwas  kveklltldna  afpflaysgi
551  pavsfcfced  tdypylgttm  dtykelieri  pelnkvaraa  aevaggfvik
601  lthdvelnld  yerynsqlls  fvrdlngyra  dikemglslq  wlysargdff
651  ratsrlttdf  gnaektdrfv  mkklndrvmr  veyhflspyv  spkespfrhv
701  fwgsgshtlp  allenlklrk  qnngafnetl  frnqlalatw  tiggaanals
751  gdvwdidnef
```

*FIG. 1B*

METHOD FOR DETECTING A MAMMAL'S PRIOR EXPOSURE TO RADIATION OR RADIOMIMETIC CHEMICALS

FIELD OF THE INVENTION

The present invention relates to methods for detecting a mammal's prior exposure to radiation or radiomimetic agents.

BACKGROUND OF THE INVENTION

There has been a continuing interest in evaluating the long-term health effects of exposure to ionizing radiation. Early studies, in the 1950's, were primarily concerned with "lower than lethality" doses. As science soon discovered, lower than lethality by no means meant harmless. In recognition of the adverse health impacts of low levels of radiation, film badges have been used as a convenient way to monitor the level of radiation exposure of individuals. By monitoring the film badge worn by an individual, the amount of radiation to which that individual was exposed while wearing the film badge was determined. These devices have practical utility when there is adequate motivation to monitor the individual's exposure level, that is, when the risk of exposure to non-trivial amounts of radiation is known in advance.

However, individuals are frequently exposed to non-trivial doses of radiation without being monitored. A number of reasons exist for non-monitoring. First, the presence of radiation may not be recognized. This is particularly true in environments where no artificial source of ionizing radiation exists, such as in the home.

However, as demonstrated by discovery of radon-rich environments, locations traditionally considered radiation-free may not be so. Second, even where the presence of radiation is recognized, its threat may not be viewed as sufficiently great to warrant monitoring. The triviality of exposure is determined in view of the dosage and frequency of exposure and the perceived danger associated with such exposure. Despite our present understanding of the danger of greater than background exposure, occasional exposures to radiation levels greater than background, such as those from medical and dental x-ray procedures, are presently not monitored. Regularly occurring exposures greater than background are considered non-trivial, and, where such exposures occur in the workplace, regulation requires that they be monitored with film badges. However, such has not always been the case. Consequently, the levels of past radiation exposure for many workers were not monitored.

For the reasons set forth above, accurate determination of cumulative past exposure for most individuals is presently impossible. Therefore, it is desirable to develop a method for determining prior exposure of an individual to radiation which does not rely on the individual having been contemporaneously monitored for exposure.

It is well documented that radiation can induce long-lived cellular alterations of the hematopoietic stem cells Akiyama et al., "Evaluation of Four Somatic Mutation Assays as Biological Dosimeter in Humans" in *Radiation Research: A Twentieth-Century Perspective*, Dewey et al., eds. Vol. II Congress Proceedings, New York: Academic Press, pp. 177-182 (1992)). Furthermore, studies have related carcinogenesis to the level of somatic mutation (McCann et al. "Detection of carcinogens as mutagens in Salmonella/microsome test: Assay of 300 chemicals," *Proc. Nat. Acad. Sci. USA*, 73:950-954 (1976); Clive et al., "Validation and characterization of the L5178Y/TK± mouse mutagen assay system," *Mutation Research*, 59:61-108 (1970)). Consequently, investigations of cumulative lifetime dosimetric methods have focussed on these stem cells and the materials produced therefrom.

Upon division, stem cells produce red blood cells, white blood cells or platelets. The identity of the cell produced and the rate of stem cell division are governed by the needs of the individual as expressed by regulatory chemicals. For example, stem cells of an individual suffering from blood loss (anemia) respond by dividing more rapidly, as well as increasing the production of red blood cells relative to white blood cells and platelets.

Several studies have focussed on the effect of prior radiation exposure on the bone marrow level of red blood cells precursors ("RBCp"). RBCp are cells produced by stem cells which are sufficiently developed to be distinguished from other cells produced by the stem cells, but which have yet to leave the bone marrow and enter the blood stream.

Gong et al., "A Method for Determining Residual Injury in the Hematopoietic System of the X-Irradiated Rat," *Radiation Research*, 37 (3):467-477 (1969) studied the level of RBCp produced in response to anemia induced by bleeding the individual animal. The anemic response, in terms of marrow level of RBCp, was depressed in individuals exposed to radiation relative to those not exposed. The study also found that the effect of radiation on anemic response was long-lived. As a function of time from radiation exposure, the depression of anemic response recovered logarithmically with a $t_{1/2}$ in rats of 30 weeks, about one-fifth of the rat lifespan.

The method, though in principle useful in determining prior radiation exposure, is impractical for assessing the extent of exposure in a large population or in humans. First, the assay requires that the patient be bled to the point of illness to induce anemic response. Second, the method requires a somewhat complicated and often painful surgical procedure to extract bone marrow from the bone of the patient. Last, because the stem cells remain localized in the region where they are irradiated (Gong et al., "Iron Kinetics Effects of 88 Millirads: Partial-Versus-Total Body X-Irradiation," *Cell Biophysics*, 13:15-27 (1988)), the method determines only radiation exposure of the bone from which the bone marrow is extracted. If the prior exposure was non-uniform over the entire body, the method fails to indicate accurately the total radiation received by the patient as a whole.

A related method for evaluating prior radiation exposure is described in Gong et al. "Effects of Low-Level (1.0 R) X-Irradiation on the Erythroid-Response of the Rat Bone Marrow," *Radiation Research*, 65:83-97 (1976), based on the observation that, in non-anemic subjects, RBCp count increases with increased radiation exposure. The method does not require inducing an anemic response, but simply involves obtaining a bone marrow sample, determining the number of RBCp therein, and correlating this number to the increased numbers of RBCp observed in irradiated individuals. Although this method does not suffer the disadvantage of requiring inducing an anemic response, it still requires a bone marrow biopsy and fails to provide accurate assessments of total radiation exposure when exposure is non-uniform over the entire body.

RBCp levels in bone marrow (both under bled and non-bled conditions) as a function of radiation exposure were quantitatively studied in Gong et al., "The Effects of Low Dose (Less than 1 Rad) X-Rays on the Erythropoietic Marrow," *Cell Biophysics*, 5:143–62 (1983) ("Gong (1983)"). The results indicate that both observed effects of radiation (i.e. non anemic RBCp elevation and suppressed anemic response) could be accurately described by a linear-logarithmic dose-response curve. Further, both techniques showed the observable effect of radiation on RPCp decreased exponentially with time from exposure, with identical half-lives.

At a minimum, all dosimeters using RBCp's have two common disadvantages: a need to obtain a bone marrow sample and the inability to determine whole body radiation exposure from a bone marrow sample. In contrast, these disadvantages do not exist when blood cells, rather than marrow cells, are used as indicators.

Both erythrocytes and lymphocytes have been the focus of a number of studies for evaluating the extent of various somatic mutations. These studies have been summarized in Akiyama et al., "Evaluation of Four Somatic Mutation Assays as Biological Dosimeter in Humans" in *Radiation Research: A Twentieth-Century Perspective*, Dewey et al., eds. Vol. II Congress Proceedings, pp. 177–182, New York: Academic Press (1992). The ability to evaluate the extent of various somatic mutations, has become increasingly important in view of a growing interest in the spectrum of mutational lesions which can occur in mammalian somatic cells and in the role of various lesions in carcinogenesis. Studies using in vitro cell systems have provided direct molecular evidence for a large number of mutational mechanisms that can lead to stable phenotypic changes in somatic cells. Since many of these mutational mechanisms have been implicated in the development of specific human tumor types, measurements of the frequency of different classes of mutagenic events in normal human cells in vivo would facilitate assessment of health risks from these events. In addition, evaluation of the extent of somatic mutations provides a means for determining prior exposure to radiation.

Wijayalaxmi et al., "Measurement of spontaneous and X-irradiation-induced 6-thio-guanine-resistant human blood lymphocytes using a T-cell cloning technique," *Mutation Research*, 125:87–94 (1984) and Sanderson et al., "Mutations in human lymphocytes: effects of X- and UV-irradiation," *Mutation Research*, 140:223–227 (1984), relate to a lymphocyte hypoxanthine quinine phosphoribosyl transferase ("HPRT") mutation assay. Results for 127 A-bomb survivors showed a statistically significant dose-related increase in the number of HPRT-deficient mutants. However, the dose-response relation is quite shallow, $2.3 \times 10^{-6}$/Gy, necessitating the sampling of a very large number of white blood cells per individual, and rendering the technique impractical for large-scale surveys. Furthermore, because of in vivo selection against the mutant lymphocytes, the effectiveness of the HPRT assay is short-lived and useful only for 1–2 years following exposure.

Kyoizumi et al., "Spontaneous loss and alteration of antigen receptor expression in mature $CD4^+$ T cell," *J. Exp. Med.*, 17:1981–1999 (1990), discloses a dosimeter based on a lymphocyte T-cell antigen receptor ("TCR") mutation assay. As is well known, most normal T-lymphocytes have surface expression of CD3 complexes, consisting of CD3 and $TCR\alpha\beta$ chain heterodimer. Since TCR genes are functionally hemizygous, when a mutation occurs in TCR genes ($\alpha$ or $\beta$), the CD3 complex cannot be expressed on the cell surface and such mutants are detected as CD3-negative cells among CD4-positive helper-inducer T-cells. The slope, about $10^{-4}$/Gy, is approximately 10 times greater than that for T-cell HPRT mutants. Another advantage of the assay is the commercial availability of monoclonal antibodies which means that the assay can be completed in several hours. However, the TCR mutant has a half-life of 2 years, and, therefore, the assay is not useful as a lifetime dosimeter. The TCR assay is further limited by inaccuracies introduced by spontaneous TCR mutations which increase with increasing age even without radiation exposure.

Recently, Turner et al., "Mutation in human lymphocytes commonly involve gene duplication and resemble those seen in cancer cells," *Proc. Natl. Acad. Sci. USA*, 85:3189–3192 (1988), have developed the lymphocyte HLA-A locus mutation assay. The assay uses monoclonal antibodies specific to HLA-A2 or HLA-A3 plus its complement to kill normal cells expressing HLA-A2 or A3 antigen on the surface. Mutant cells lacking the antigen survive. The dose-response relation is reportedly $3.1 \times 10^{-5}$/Gy. The half-life of the mutants, however, is approximately that of the TCR mutants. Therefore, the HLA-A mutation assay is not suitable for use as a lifetime dosimeter.

All these methods which use white blood cells require a large sample of blood, because only 0.01% of blood cells are white cells. This disadvantage, in addition to the short-lived nature of these assays, has been overcome, to some degree, by Langlois et al., "Measurements of the frequency of human erythrocytes with gene expression loss phenotypes at a glycophorin A locus," *Hum. Genet.* 74:353–362 (1986). Langlois determines prior exposure by detecting the loss of gene expression at the glycophorin A locus in human somatic cells. Glycophorin A ("GPA"), a cell-surface sialoglycoprotein on erythrocytes, occurs in two allelic forms, M and N and is the product of codominantly expressed alleles on chromosome 4. In the GPA expression-loss assay, pairs of monoclonal antibodies specific for individual allelic forms are each conjugated with a different fluorescent dye and used to label fixed erythrocytes from heterozygous MN donors. Flow cytometry and sorting are used to enumerate and purify rare, single-color cells that lack the expression of one of the two GPA alleles. Presumably, these cells lack expression because they are progeny of mutated erythroid precursor cells. The GPA assay revealed a persistent presence of a stem cell mutation approximately 50 years after irradiation, which makes it the only presently available mutation assay system having potential to be used as a lifetime dosimeter.

However, the assay has limitations. One drawback relates to uncertainty in the high dose limit. Since the assay measures the presence of GPA protein and since GPA decreases with increasing exposure, statistical error increases with increasing dose. At high doses, where loss of gene expression is essentially complete and where there are vanishingly few cells expressing GPA, statistical anomalies become overriding factors. Another disadvantage is that the GPA assay is useful only in individuals who are heterozygous for the MN blood type, which is only about 50% of the human population. Furthermore, the GPA assay requires that 5 million cells be counted to identify between 20 and 900 variant GPA cells in an exposure range of 0 to 300 cGy. Because of the limitations of the cell cytometry technology, each sample takes approximately ½ hour to complete. This counting time, though short relative to the counting times encountered in the lymphocyte assays, discussed above, makes the GPA method unsuitable for screening large populations.

Therefore, there remains a need for a lifetime biological dosimetry process that is based on a readily available body fluid, that is uniformly sensitive to dose over the range from 0 to 600 cGy, and that is suitable for screening of large populations.

SUMMARY OF INVENTION

One aspect of the present invention relates to a method for detecting a mammal's prior exposure to radiation or radiomimetic agents. The process involves providing a sample of red blood cells from a mammal. The red blood cells have a quantity of transferrin receptors. The quantity of transferrin receptors on the red blood cells is detected and then correlated to the mammal's prior exposure to radiation or radiomimetic agents.

Another aspect of the present invention relates to a method for detecting a mammal's prior exposure to radiation or radiomimetic agents. In this process, a sample of red blood cells from a mammal is provided. The red blood cells include a protein whose quantity increases with increasing exposure of the mammal to radiation or radiomimetic agents. The quantity of this protein on the red blood cells is detected, and this quantity is then correlated to the mammal's prior exposure to radiation or radiomimetic agents.

The present invention also pertains to a method for detecting a mammal's prior exposure to radiation or radiomimetic agents. The process involves providing a sample of red blood cells from a mammal. The red blood cells have a quantity of a protein encoded by a nucleotide sequence within the DNA locus which contains the gene encoding transferrin receptor. The quantity of this protein on the red blood cells of the sample is detected, and this quantity is correlated to the mammal's prior exposure to radiation or radiomimetic agents.

The present invention is also directed to a method for detecting a mammal's prior exposure to radiation or radiomimetic agents. The method includes providing a sample of nucleic acids from a cell produced by a hematopoietic stem cell. The nucleic acids have a quantity of mutations which cause expression of transferrin receptor in mature erythrocytes. The quantity is detected and is then correlated to the mammal's prior exposure to radiation or radiomimetic agents.

The methods of the present invention can be used to detect the cumulative amount of radiation or radiomimetic agents to which a mammal was exposed in the past. The ability to assess accurately the cumulative lifetime radiation exposure of an individual is critical in studying the effects of radiation, especially cancer risk and other delayed responses. Until now, only populations exposed to high or moderate doses could be studied, because only individuals from these populations were monitored for radiation exposure. In such studies, the effects of low dose radiation were predicted by extrapolation from high or moderate dose studies. With the present invention, researchers are able to assess accurately cumulative lifetime exposure and, therefore, are able to directly study the effect of low doses of radiation.

The ability to assess cumulative exposure is also useful in evaluating whether there is a continuing exposure to radiation or radiomimetic agents, and if there is, to evaluate the level of such exposure. Thus, the method can also be used as a monitor of industrial, medical, military, and even environmental exposure and can be used to determine whether additional precautions should be taken to reduce exposure.

Certain features of the method of the present invention make it useful and particularly suited for studying cumulative lifetime exposure of large populations. First, the methods of the present invention are applicable to all individuals and do not depend on an individual's belonging to a particular genetic group. Second, the test is convenient for the subjects. It requires only approximately 5 μl of blood and does not require dietary restriction on the part of the individual prior to the test. The limited amount of blood necessary permits the test to be conducted as frequently as desired. The test is also advantageous, because it requires no special handling of the sample, uses reagents which are stable and have an extended shelf life, and can be conducted using freshly obtained blood or blood which has been stored.

Furthermore, the test's sensitivity, extending from 0.1 cGy to over 600 cGy, spans both the environmental and the lethal dose ranges. This suggests that the method is applicable as a universal diagnostic test for all nuclear events, from environmental contaminations to nuclear holocausts.

BRIEF DESCRIPTION OF THE DRAWINGS

FIGS. 1A and 1B depict the amino acid sequences for rat (Rattus norvegicus, GenInfo ID. No. 112425) and human (Homo sapiens, GenInfo ID. No. 136378) transferrin receptor.

DETAILED DESCRIPTION

Figure 2:
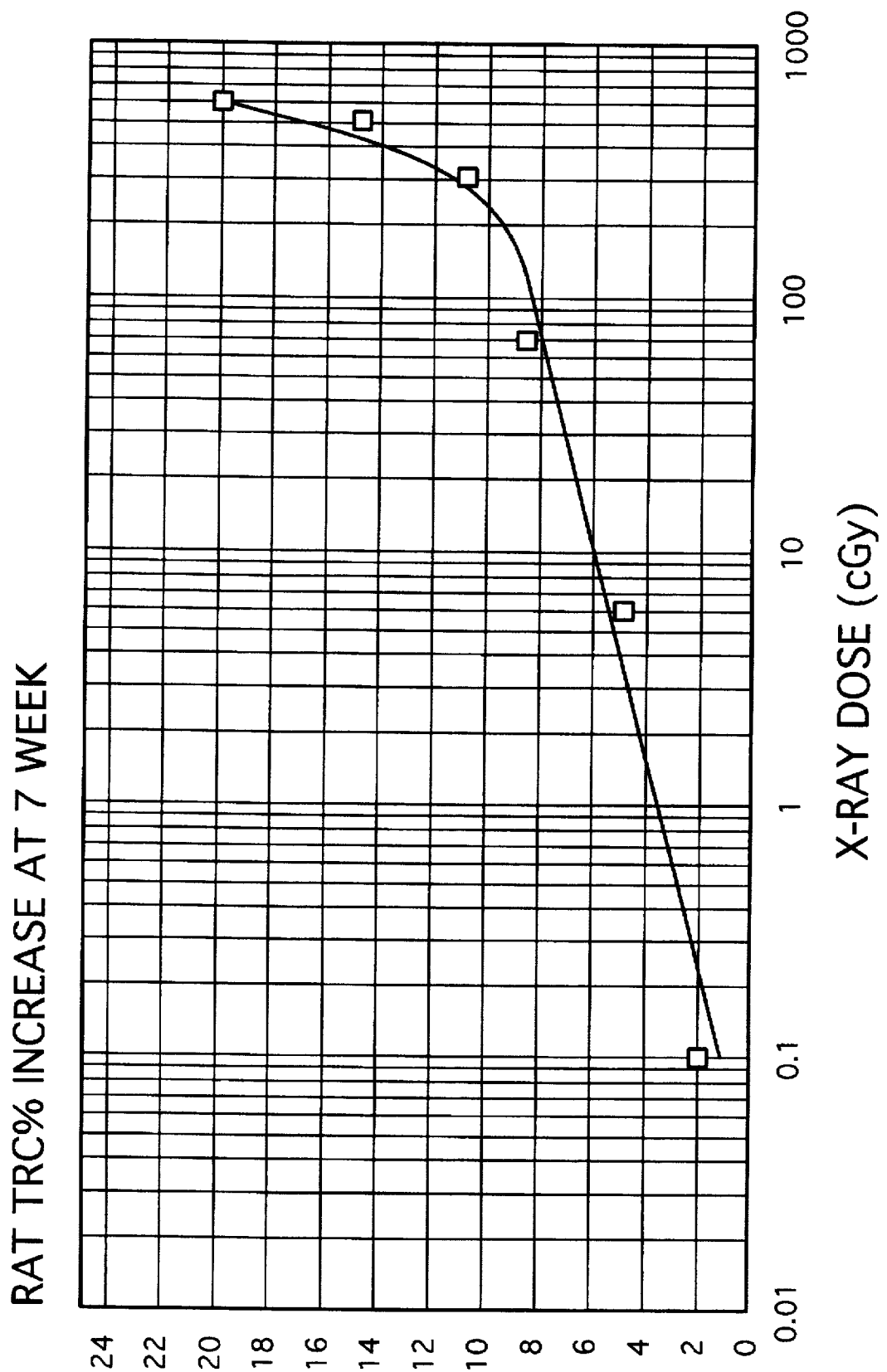
FIG. 2 is a semi-log plot of the increase in the quantity of cells having a quantity of transferrin receptor thereon greater than an arbitrary number (i.e., increase in the quantity of "marked cells") versus radiation dose showing the effects of x-ray radiation on the quantity of transferrin receptor in red blood cells in rats at 7 weeks post irradiation. The line represents the mathematical expression: $y=a+b(\log x)$, for doses between 0.1 and 150 cGy, and $y=c+dx+fx^2$ for doses between 150–600 cGy, where y is the increase in the quantity of marked cells (expressed as percent), x is the dose, and a, b, c, d, and f are 3.56, 2.31, 8.54, −0.00327, and 0.0000378, respectively.

The present invention is directed to a method for detecting a mammal's prior exposure to radiation or radiomimetic agents. The method includes providing a sample of red blood cells from a mammal. The red blood cells have a quantity of a protein thereon and this quantity is detected and then correlated to the mammal's prior exposure to radiation or radiomimetic agents. The protein can be any protein whose quantity increases with increasing exposure of the mammal to radiation or radiomimetic agents.

Proteins whose quantity increases with increasing exposure of the mammal to radiation or radiomimetic agents can be identified in a number of different ways.

If the protein is one that has been described in the literature and if a commercial monoclonal antibody ("mAb") is available to specifically recognize the protein, for example, an immunofluorescence based assay can be used to a) detect the protein on the cell surface of the red blood cells and b) to quantitate the amount of the cell surface bound fluorescenated secondary antibody:primary monoclonal antibody complex by monitoring fluorescent emissions spectrofluorophotometrically. The assay can be performed by conventional methodologies such as those described in Harlow, et al., ed., *Antibodies: A Laboratory Manual,* Cold Spring Harbor, N.Y.: Cold Spring Harbor Press (1988) ("Harlow"), which is hereby incorporated by reference. Standardization of the assay to determine fluorescent emission per cell surface protein, permits indirect quantification of such cell surface protein.

If the protein is unknown, or if the protein is a variant form of a known protein such that the binding portion of the protein is not recognized by a commercial mAb, mAbs and polyclonal antibodies can be developed against the new protein following standard protocols as described by Harlow, which is hereby incorporated by reference. These antibodies can be used as described above to quantitate the amount of radiation/radiomimetic agent-induced cell surface protein.

If the cell surface protein is a variant form, this might indicate either differential RNA splicing (Cotner et al., *Blood* 73:214–221 (1989) and Tyler et al., *Nature* 293:406–408 (1981), which are hereby incorporated by reference) or an aberrant protein. Differential mRNA species can be generated through alternative mRNA splicing, and an aberrant protein would indicate the presence of a mutation in the protein coding nucleic acid sequence. Differential mRNA splicing would be detected upon a Northern blot analysis; a mutation present in the coding region of a gene is transcribed into a novel mRNA species, which can be detected by Northern blot analysis as described in Sambrook et al., *Molecular Cloning: A Laboratory Manual,* 2nd edition, Cold Spring Harbor, N.Y.: Cold Spring Harbor (1989) ("Sambrook"), which is hereby incorporated by reference. Briefly, total RNA extracted from irradiated and control erythroid progenitor cells is size fractionated using gel electrophoresis. The RNA is immobilized on a nylon membrane and hybridized with a labeled cDNA probe. The probe can be, for example, radiolabeled, in which case autoradiography can be used to produce bands which indicate the number and size of the mRNA species complementary to the probe. mRNA species from irradiated and non-irradiated cells, detected by Northern analysis, are then compared to determine whether or not a novel mRNA species is transcribed in the irradiated cells. If novel mRNA species are detected, a reverse-transcription polymerase chain reaction ("RT-PCR") can be developed to routinely screen for these nucleic acid sequence alterations. This assay has the advantage of increased sensitivity and faster turn-around time.

For example, cDNA probes to those genes involved in the regulation of aberrant transferrin receptor on the mature erythrocyte can be used in Northern analyses to screen for novel mRNA species. The generation of consistent, unique mRNA species in RNA extracted from irradiated cells can be used to routinely screen for the presence of these mutations. A mutation is an alteration of the normal DNA sequence which may be caused by, for example, the presence of point mutations, deletions, insertions, duplications, gene amplifications, and translocations. A mutation in the coding region of a gene is transcribed into a mRNA, but the nature of the mutation will determine if a novel mRNA species is detected by Northern analysis. For example, a point mutation would not be detected by Northern analysis, because the overall size of the coding region would remain the same and because Northern analysis only reveals relatively major sequence differences. Thus, the overall size of the mRNA species, relative to the number of nucleotides involved in the mutation, will determine whether or not a novel mRNA species is detected. Therefore, the inability to detect a novel mRNA species does not exclude the presence of a mutation. The detection of any mRNA species is dependent upon the transcriptional activity of the gene: if a gene is silent at the time of the analysis, mRNA will not be transcribed. Newly transcribed RNA can be identified, for example, using conventional nuclear runoff transcription assays, such as those described in Cairo et al., *J. Biol. Chem.* 269:6405–6409 (1994) ("Cairo"), Chan et al., *Eur. J. Biochem.* 220:683–692 (1994) ("Chan"), and Ausubel et al., eds., *Current Protocols in Molecular Biology,* Green and Wiley (1992), which are hereby incorporated by reference. The assay permits direct measurement and comparison of specific gene transcription in cells under various conditions. In the present invention, erythroid or myeloid progenitor cells can be irradiated and, at intervals post-irradiation, the nuclei can be isolated and analyzed. Briefly, nascent RNA transcripts can be labeled (such as radiolabeled) and can be used to detect specific RNA transcripts by hybridization to cDNAs immobilized on membranes. Those cDNAs containing complementary sequences are identified by standard methods, such as autoradiography.

Alternatively or additionally, Southern analyses can be performed on DNA extracted from irradiated erythroid progenitor cells and "normal" erythroid progenitor cells to screen for the presence of a mutation in the gene encoding the protein whose quantity increases with increasing exposure to radiation or radiomimetic agents, or in a related gene (Sambrook, which is hereby incorporated by reference). Briefly, restricted DNA is fractionated in agarose gels, immobilized onto nylon membranes, and hybridized with labeled cDNA or oligonucleotide probes. Using a radiolabeled probe and autoradiography, the specific fragment or fragments containing complementary sequences can be detected. Mutations will be displayed by the appearance of unique restricted fragment length polymorphisms ("RFLPs"). If the DNA sequence alteration (mutation) is found to cosegregate with the phenotype described in this invention, then a Southern analysis may result in a precise and reproducible pattern of bands representing the DNA fragment(s) containing the wild-type (normal) and mutated genes. The restricted DNA can also be hybridized with probes (e.g., cDNA or oligonucleotide probes) of those genes identified, candidates, and those yet to be discovered, involved in the regulation of expression of the protein of the present invention. The generation of consistent, unique RFLPs in DNA extracted from irradiated cells can be used as a means to routinely screen for the presence of these mutations. If novel RFLPs are generated, a PCR-based assay can be developed to routinely screen for the presence of these mutations. This assay has the advantage of using a maximum of 1 µg DNA per primer set, compared with 30 µg for a Southern analysis. Southern analysis also requires high molecular weight genomic DNA, which is not a requirement for a PCR based assay.

Southern analysis can be used to reveal relatively major sequence differences, as detected by restriction endonuclease digestion. Therefore, similar to a Northern analysis, the nature of the mutation will dictate whether or not a mutated gene is detected. In the absence of observed mutations via Southern or Northern analyses, other methodologies can be exploited to detect sequence alterations. Methods to screen for mutations include, for example, analyzing mismatched heteroduplexes of complementary DNA strands derived from wild-type and mutant sequences, RNAse protection assays, exon scanning, genomic subtraction, and polymerase chain reaction ("PCR") based assays, such as single-strand conformational polymorphism ("SSCP") analysis, allele-specific PCR, oligoligation assays, and transcription-based PCR assays (Bernstam, *Handbook of Gene Level Diagnostics in Clinical Practice*, Boca Raton: CRC Press (1992), Landegren, *Genetic Analysis Techniques and Applications* 9:3–8 (1992), and Sambrook, which are hereby incorporated by reference).

Each mutation, irrespective of the detecting methodology used, is characterized and sequenced. The nature of the mutation will ultimately determine the methodology of routine screening and the diagnostic assay designed to rapidly detect, distinguish, and quantitate the known sequence variations. These assays may involve, for example, Northern or Southern analyses, transcription-based amplification assays (chemical or enzymatic), or DNA amplification-based assays (chemical or enzymatic). Alternatively, hybridization assays, such as branched DNA signal amplification, in which the probe carries an exceptionally high specific labeling activity, such that it can hybridize and allow detection of a non-amplified low target copy number, can be used (Wilbur et al. In: *Molecular Methods for Viral Detection*, Academic Press, (1995), which is hereby incorporated by reference). Mutated genes can be analyzed as mRNA molecules or genomic DNA, which may not be mutually exclusive. In these assays, the mutation acts as a highly specific marker, present in only those erythroid progenitor cells exposed to radiation.

In the absence of sequence alterations in either genomic DNA or mRNA, post-transcriptional changes may be involved. This can be examined by gel retardation/gel shift mobility assays where RNA-protein complexes are analyzed (Leibold et al., *Proc. Natl. Acad. Sci. USA* 85:2171–2175 (1988) and Jaffrey et al., *Nucleic Acid Res.* 21:4627–4631 (1993), which are hereby incorporated by reference). Briefly, erythroid or myeloid progenitor cells are irradiated and cytoplasmic lysates prepared. RNA transferrin receptor transcripts of the protein-binding regions are then synthesized and labeled, such as with a radiolabel. The binding reactions are carried out with the cytoplasmic lysates and the labeled RNA. After incubation, the material is loaded onto a non-denaturating polyacrylamide gel, and RNA binding proteins are detected by their ability to retard the mobility of labeled (e.g., radiolabeled) RNA electrophoresed through the gel. The gel is dried, and the label is detected (e.g., by autoradiography). In the absence of binding proteins, the unbound labeled RNA migrates freely through the gel and shows as a single band. In the presence of a binding protein, the RNA:protein complex moves more slowly than the band corresponding to RNA alone and additional bands are detected. After detection of a RNA binding protein, the protein can be purified using standard chromatography techniques.

If the increase in the quantity of the protein with increasing radiation or radiomimetic exposure is attributed to a functional mutation, the mutated gene can be cloned into a gene expression system (Sambrook, which is hereby incorporated by reference), such that the large quantities of the aberrant protein are produced. The protein can then be used to raise antibodies following standard techniques (Harlow, which is hereby incorporated by reference), and the antibodies can be used in a simple screening assay for the detection and quantitation of the aberrant protein on red blood cells.

Cytogenetic analysis can also be performed on the irradiated stem cells to determine the physical characteristics of the chromosomes. This analysis can be used to identify the elements which cause increased protein expression upon exposure to radiation or radiomimetic agents, such as gene amplification, chromosomal translocation, generation of double minutes, chromosomal insertions or deletions, or any other aberrant chromosomal structure. The mutation may result in a mutant protein or in abnormal persistence of a normal protein.

The protein can be transferrin receptor. Transferrin receptor is a surface protein which binds iron and makes it available to the cell during hemoglobin synthesis. It is present on early erythroid cells of all mammals but, generally, is lost as reticulocytes differentiate into mature erythrocytes. However, erythrocytes produced by bone marrow cells exposed to radiation or radiomimetic agents retain transferrin receptor in amounts that correlate to the exposure. The retained transferrin can be normal, non-mutated transferrin receptor or mutated transferrin receptor. By mutated transferrin receptor is meant any molecule sufficiently similar to normal, non-mutant transferrin receptor so as to be reactive with antibodies or probes which react with normal, non-mutated transferrin receptor. In rats, normal, non-mutated transferrin receptor has the amino acid sequence depicted in FIG. 1A. Normal, non-mutated human transferrin receptor has the amino acid sequence shown in FIG. 1B and is encoded by the human gene 3q26.2-qter, 31 kb, as described by Kuhn et al., *Cell* 37:95–103 (1984), which is hereby incorporated by reference.

The protein can also be any protein encoded by a nucleotide sequence within the locus which contains the gene encoding transferrin receptor. For example, a human's prior exposure to radiation or radiomimetic agents can be detected by using any protein encoded by a gene contained in human 3q26.2→qter. Examples of such proteins include those identified in McClelland et al., *Cell* 39:267–274 (1984) ("McClelland"), which is hereby incorporated by reference.

Although specific loci which encode transferrin receptor for humans has been provided herein, this is for illustration purposes only. Loci encoding transferrin receptor in other mammalian species are described in Stearne et al, *J. Immunol.* 134:3474–3479 (1985), which is hereby incorporated by reference.

Alternatively, the locus encoding transferrin receptor for a mammal can be determined by screening genomic libraries using the protocols described in Sambrook, which is hereby incorporated by reference. More particularly, monoclonal antibodies can be used for expression cloning as described in Kuhn et al., *Cell* 37:95–103 (1984) and Rubin et al., *Am. J. Hum. Genet.* 37:1112–1116 (1985), which are hereby incorporated by reference. Briefly, high molecular weight mammalian DNA and plasmid DNA containing a drug resistant gene (e.g., lacz), are cotransfected into mammalian cells. Transfectants are selected upon incubation in the presence of an antibiotic (e.g., geneticin), which can only be metabolized by cells containing the drug resistant gene (e.g., lacz). Transfectants are stained with the appropriate monoclonal antibody and fluorescenated with a secondary antibody. Cell sorting by fluorescence activated cell sorter ("FACS") permits selection of those cells expressing the protein. These cells are cloned, and the amount of transferred mammalian DNA is determined. DNA from the cell line containing the smallest fragment of mammalian DNA is used to construct a phage library. The library is screened by filter hybridization with radiolabeled mammalian DNA to isolate those phages with mammalian DNA. The mammalian inserts contained therein, are restricted and screened for their ability to bind the monoclonal antibody. In this way, the coding region of the gene is located. Unique fragments from within the coding region are radiolabeled and used as probes in a Northern analysis to detect and size the mRNA species. Screening a cDNA library confirms the size of the mRNA species. To determine the size of the gene and to locate coding and intervening sequences, the cDNA is hybridized to restricted fragments of the genomic recombinant phage DNAs. The gene locus is chromosomally mapped by in situ hybridization. This involves radiolabeling a cDNA probe to a very high specific activity and hybridizing to cells arrested in metaphase in such a way that each chromosome is distinguishable under a light microscope. Autoradiography is then used in conjunction with chromosome staining (e.g., G-banding) to reveal directly to which band on which chromosome the probe is hybridized (Rabin et al, Am. J. Hum. Genet. 37:1112–1116 (1985), which is hereby incorporated by reference).

Once the locus encoding transferrin receptor has been identified, other proteins which are encoded by genes within that locus receptor can be determined by the procedures described by McClelland, which is hereby incorporated by reference. Briefly, cDNA is sequenced, and, from this sequence, the amino acid sequence is deduced. The amino acid sequence is then analyzed to determine, for example, hydrophobic membrane-spanning regions and cytoplasmic anchors for transmembrane receptors. Thus, the structure and probable function of a protein can be predicted from its amino acid residue sequence. Amino acid sequence homology searches can also be used to determine if the protein has complete or partial homology to other proteins. Proteins encoded by the locus encoding transferrin receptor, in other mammalian species are listed in Towbridge et al., *Biochem. Pharmacol.* 33:925–930 (1984) and Agthoven et al., *Eu. J. Biochem.* 140:433–440 (1994), which are hereby incorporated by reference.

The sample of red blood cells can be provided by any conventional method for removing blood from mammals, such as, for example, by drawing it under suction through a needle or by lancing the skin. The size of the sample should be such that more than 1000 red blood cells are contained therein. Although this size of sample will give only a very crude indication of prior exposure, even this small sample can be sufficient to reliably discern between individuals exposed to 10 cGy from those exposed to 600 cGy. Preferably, the sample contains more than 5,000 cells, more preferably, between 10,000 and 20,000 red blood cells. In most mammals, freshly drawn blood contains about 8 million red blood cells/µl. Consequently, a freshly drawn sample preferably has a minimum volume between 1250 and 2500 picoliters. The sample can be provided from a larger sample obtained for other purposes, such as for a standard hematological analysis. The blood may have been drawn previously and stored for a period of time prior to using it in the method of the instant invention. The length of time the blood may be stored prior to use depends on its storage conditions. Red blood cells can be stored at −70° C. for 1 year or at 4° C. for 42 days. Alternatively, the blood can be stored at 4° C. for up to 6 weeks without altering the results of the method using buffered formalin or other standard blood fixation methods, such as those described in *American Association Blood Banks Technical Manual*, 13th edition, Walker, ed (1995), which is hereby incorporated by reference.

The quantity of protein on the red blood cells from the sample thus provided can be detected by a number of different methods. Some methods rely on purifying the protein of interest prior to detecting the quantity present. Briefly, the cell is lysed, the proteins removed from other cellular debris, and the protein of interest separated from other proteins by SDS-PAGE, ELISA, adsorption chromatography, affinity chromatography, size-exclusion chromatography, and density gradient centrifugation. The amount of protein, thus separated, can be quantified, for example, by treating it with a label, such as a fluorescent or radioactive label, and measuring the appropriate emission. Where the protein is transferrin receptor the amount of separated protein present can also be determined by monitoring $Fe^{3+}$ absorbance spectrophotometrically.

Other methods for detecting the quantity of protein on the red blood cells rely on selectively marking the protein while on the red blood cell and counting the number of markers present. For example, the sample can be contacted with an antibody, a binding portion thereof, or a probe recognizing the protein. After a time sufficient to permit a quantity of the antibody, binding portion thereof, or probe to bind with the protein on the red blood cells, the quantity of antibody, binding portion thereof, or probe bound to the protein is determined. By relating the quantity of the bound antibody, binding portion thereof, or probe to the quantity of protein on the red blood cells of the sample, the quantity of protein on the red blood cells of the sample is detected.

Antibodies suitable for marking the protein can be monoclonal or polyclonal. In addition, fragments, half-antibodies, hybrid derivatives, and probes may be utilized.

Monoclonal antibody production may be effected by techniques which are well-known in the art. Basically, the process involves first obtaining immune cells (lymphocytes) from the spleen of a mammal (e.g., mouse) which has been previously immunized with the antigen of interest either in vivo or in vitro. The antibody-secreting lymphocytes are then fused with (mouse) myeloma cells or transformed cells, which are capable of replicating indefinitely in cell culture, thereby producing an immortal, immunoglobulin-secreting cell line. The resulting fused cells, or hybridomas, are cultured, and the resulting colonies screened for the production of the desired monoclonal antibodies. Colonies producing such antibodies are cloned, and grown either in vivo or in vitro to produce large quantities of antibody. A description of the theoretical basis and practical methodology of fusing such cells is set forth in Kohler et al., "Continuous cultures of fused cells secreting antibody of predefined specificity," *Nature* 256:495 (1975), which is hereby incorporated by reference.

Mammalian lymphocytes are immunized by in vivo immunization of the animal (e.g., a mouse) with the protein or polypeptide of the present invention. Such immunizations are repeated as necessary at intervals of up to several weeks to obtain a sufficient titer of antibodies. The virus is carried in appropriate solutions or adjuvants. Following the last antigen boost, the animals are sacrificed and spleen cells removed.

Fusion with mammalian myeloma cells or other fusion partners capable of replicating indefinitely in cell culture is effected by standard and well-known techniques, for example, by using polyethylene glycol ("PEG") or other fusing agents (See Milstein et al., "Derivation of specific antibody-producing tissue culture," *Eur. J. Immunol.* 6:511 (1976), which is hereby incorporated by reference). This immortal cell line, which is preferably murine, but may also be derived from cells of other mammalian species, including but not limited to rats and humans, is selected to be deficient in enzymes necessary for the utilization of certain nutrients, to be capable of rapid growth and to have good fusion capability. Many such cell lines are known to those skilled in the art, and others are regularly described.

Procedures for raising polyclonal antibodies are also well known. Typically, such antibodies can be raised by administering the protein or polypeptide of the present invention subcutaneously to New Zealand white rabbits which have first been bled to obtain pre-immune serum. The antigens can be injected at a total volume of 100 µl per site at six different sites. Each injected material will contain synthetic surfactant adjuvant pluronic polyols, or pulverized acrylamide gel containing the protein or polypeptide after SDS-polyacrylamide gel electrophoresis. The rabbits are then bled two weeks after the first injection and periodically boosted with the same antigen three times every six weeks. A sample of serum is then collected 10 days after each boost. Polyclonal antibodies are then recovered from the serum by affinity chromatography using the corresponding antigen to capture the antibody. Ultimately, the rabbits are euthanized with pentobarbital 150 mg/Kg IV. This and other procedures for raising polyclonal antibodies are disclosed in Harlow et. al., ed., *Antibodies: A Laboratory Manual*, Cold Spring Harbor, N.Y.: Cold Spring Harbor Press (1988), which is hereby incorporated by reference.

In addition to utilizing whole antibodies, the processes of the present invention encompass use of binding portions of such antibodies. Such binding portions include Fab fragments, F(ab')$_2$ fragments, and Fv fragments. These antibody fragments can be made by conventional procedures, such as proteolytic fragmentation procedures, as described in Goding, *Monoclonal Antibodies: Principles and Practice*, pp. 98–118 New York:Academic Press (1983) ("Goding"), which is hereby incorporated by reference.

Alternatively, the processes of the present invention can utilize probes found in nature or prepared synthetically from recombinant DNA procedures or other biological procedures. Suitable probes are molecules which bind to the above-identified protein or nucleic acid sequences. Such probes can be, for example, native proteins or proteins generated from mutated nucleotide sequences, including entire mutated genes, and cDNAs.

Where the protein is transferrin receptor, monoclonal antibodies for many mammalian species are commercially available. For example, monoclonal antibodies human anti-CD71, rat anti-CD71, and mouse anti-CD71, recognizing human, rat, and mouse transferrin receptor, are available from Becton-Dickinson (San Jose, Calif.), Chemicon International, Inc. (Temecula, Calif.), and BioSource (Camarilla, Calif.).

The antibodies, binding portions thereof, or probes are utilized to detect the quantity of the protein on the red blood cells of the sample. This is preferably achieved by labeling the antibody, binding portion thereof, or probe, contacting the labeled antibody, binding portion thereof, or probe with the sample, and then detecting the label. Suitable labels include radiolabels, such as $^{131}$I, $^{111}$In, $^{123}$I, $^{99m}$Tc, $^{32}$P, $^{125}$I, $^{3}$H, and $^{14}$C, fluorescent labels, such as fluorescein and rhodamine, nuclear magnetic resonance active labels, and chemiluminescers, such as luciferin.

Preferably, the antibody is a monoclonal antibody selected from the group consisting of a radiolabeled monoclonal antibody, a fluorescent monoclonal antibody, and mixtures thereof. The antibody can be labeled with such reagents using techniques known in the art. For example, see Wensel et al., *Radioimmunoimaging and Radioimmunotherapy*, New York:Elsevier 1983), which is hereby incorporated by reference, for techniques relating to the radiolabeling of antibodies. See also, Colcher et al., "Use of Monoclonal Antibodies as Radiopharmaceuticals for the Localization of Human Carcinoma Xenografts in Athymic Mice", *Meth. Enzymol.* 121:802–816 (1986), which is hereby incorporated by reference.

The specific activity of a tagged antibody, fragment thereof, or probe depends upon the half-life, the isotopic purity of the radioactive label, and the method by which the label is incorporated into the antibody, fragment thereof, or probe. Table 1 lists several common isotopes, their specific activities, and their half-lives. In immunoassay tests, the higher the specific activity, in general, the greater the sensitivity.

TABLE 1

| Isotope | Specific Activity of Pure Isotope (Curies/mole) | Half-Life |
| --- | --- | --- |
| $^{14}$C | $6.25 \times 10^1$ | 5720 years |
| $^{3}$H | $2.01 \times 10^4$ | 12.5 years |
| $^{35}$S | $1.50 \times 10^6$ | 87 days |
| $^{125}$I | $2.18 \times 10^6$ | 60 days |
| $^{32}$P | $3.16 \times 10^6$ | 14.3 days |
| $^{131}$I | $1.62 \times 10^7$ | 8.1 days |

Procedures for labeling antibodies, binding portions thereof, or probes with the radioactive isotopes listed in Table 1 are generally known in the art. Tritium labeling procedures are described in U.S. Pat. No. 4,302,438, which is hereby incorporated by reference. Iodinating, tritium labeling, and $^{35}$S labeling procedures especially adapted for murine monoclonal antibodies are described by Goding (pp. 124–126) and the references cited therein, which are hereby incorporated by reference. Other procedures for producing iodinated antibodies are described by Hunter et al., *Nature* 144:945 (1962), David et al., *Biochemistry* 13:1014–1021 (1974), and U.S. Pat. Nos. 3,867,517 and 4,376,110, which are hereby incorporated by reference. Radiolabeling elements which are useful in imaging include $^{123}$I, $^{131}$I, $^{111}$In, and $^{99m}$Tc, for example. Procedures for iodinating antibodies are described by Greenwood et al., *Biochem. J.* 89:114–123 (1963); Marchalonis, *Biochem. J.* 113:299–305 (1969); and Morrison et al., *Immunochemistry*, 289–297 (1971), which are hereby incorporated by reference. Procedures for $^{99m}$Tc-labeling re described by Rhodes, B. et al. in Burchiel et al. (eds.), *Tumor Imaging: The Radioimmunochemical Detection of Cancer*, New York:Masson 111–123 (1982) and the references cited therein, which are hereby incorporated by reference. Procedures suitable for preparing $^{111}$In-labeling antibodies are described by Hnatowich et al., *J. Immul. Methods*, 65:147–157 (1983), Hnatowich et al., *J. Applied Radiation*, 35:554–557 (1984), and Buckley, R. et al., *F.E.B.S.* 166:202–204 (1984), which are hereby incorporated by reference.

Fluorophore and chromophore labeled antibodies, binding portions thereof, or probes can be prepared from standard moieties known in the art. Since antibodies and other proteins absorb light having wavelengths up to about 310 nm, the fluorescent moieties should be selected to have substantial absorption at wavelengths above 310 nm and preferably above 400 nm. A variety of suitable fluorescers and chromophores are described by Stryer, *Science*, 162:526 (1968) and Brand, L. et al., *Annual Review of Biochemistry*, 41:843–868 (1972), which are hereby incorporated by reference. The antibodies, binding portions thereof, or probes can be labeled with fluorescent chromophore groups by conventional procedures such as those disclosed in U.S. Pat. Nos. 3,940,475, 4,289,747, and 4,376,110, which are hereby incorporated by reference.

One group of fluorescers having a number of the desirable properties described above are the xanthene dyes, which include the fluoresceins derived from 3,6-dihydroxy-9-phenylxanthhydrol and resamines and rhodamines derived from 3,6-diamino-9-phenylxanthydrol and lissanime rhodamine B. The rhodamine and fluorescein derivatives of 9-o-carboxyphenylxanthhydrol have a 9-o-carboxyphenyl group. Fluorescein compounds having reactive coupling groups, such as amino and isothiocyanate groups, such as fluorescein isothiocyanate and fluorescamine, are readily available. Another group of fluorescent compounds are the naphthylamines, having an amino group in the $\alpha$ or $\beta$ position.

Antibodies or binding portions thereof or probes can be labeled with fluorochromes or chromophores by the procedures described by Goding (supra, pp 208–249), which is hereby incorporated by reference. The antibodies or binding portions thereof or probes can be labeled with an indicating group containing the NMR-active $^{19}F$ atom, or a plurality of such atoms inasmuch as (i) substantially all of naturally abundant fluorine atoms are the $^{19}F$ isotope and, thus, substantially all fluorine-containing compounds are NMR-active; and (ii) many chemically active polyfluorinated compounds such as trifluoroacetic anhydride are commercially available at relatively low cost. Antibodies or binding portions thereof or probes can also be labeled with compounds whose presence can be detected chemically, spectrophotometrically, visually, electrically, or electrochemically, such as, for example, dyes, pigments, metal ions, dye-coupling agents, and metallic colloids.

In particular, CD71, clone L01.1, derived from the hybridization of mouse P3-X63-Ag8.653 myeloma cells with spleen cells from BALB/c mice immunized with blast cells from pokeweed mitogen-stimulated peripheral blood cells in accordance with the method of Judd et al, "Novel surface antigens expressed on dividing cells but absent from non-dividing cells," *J. Exp. Med.*, 11:579–586 (1979), which is hereby incorporated by reference, labeled with FITC, available commercially from Becton Dickinson (San Jose, Calif.), is especially useful in detecting transferrin receptor in humans. Suitable human, rat, and mouse CD71 antibodies have EMBL/GENBANK accession numbers X01060, M58040, and M29618, respectively. These antibodies are further described, in terms of preparation and use, in Schneider et al., *Nature*, 311:675–678 (1984), Roberts et al., *Mol. Cell Endocrinol.* 14:531–542 (1985), and Stearne et al., *J. Immunol.* 134:3474–3479 (1985), which are hereby incorporated by reference.

Contacting the sample containing the red blood cells with the antibody, binding portion thereof, or probe can be done in bulk, such as, by mixing the red blood cells with a solution containing an excess of the antibody, binding portion thereof, or probe and incubating the mixture for a period of time sufficient to permit the antibody, binding portion thereof, or probe to bind with the protein. Unbound (i.e., excess) antibody, binding portion thereof, or probe is then removed, for example, by dialysis, exclusion chromatography, filtration, ultrafiltration, or centrifugation. The quantity of bound antibody, binding portion thereof, or probe is determined either indirectly, by measuring the quantity of antibody, binding portion thereof, or probe removed, or directly, by measuring the quantity of antibody, binding portion thereof, or probe retained by the cells after removal of the unbound antibody, binding portion thereof, or probe. In either case, if the antibody, binding portion thereof, or probe is labeled, the quantity of antibody, binding portion thereof, or probe is determined by measuring the amount of label present, for example, by fluoroscopy or by radiometry. Where the antibody, binding portion thereof, or probe is not labeled, the amount of antibody, binding portion thereof, or probe present can be determined by adding a labeled agent, which reacts with the antibody, binding portion thereof, or probe, to the blood sample containing the bound antibody, binding portion thereof, or probe. The addition is conducted under conditions effective to permit a quantity of the labeled agent to react with and bind to the quantity of bound antibody, binding portion thereof, or probe. The quantity of labeled agent bound to the antibody, binding portion thereof, or probe is ascertained by methods appropriate for the label employed. For example, where the agent is fluorescent, the quantity of labeled agent can be ascertained by exciting the agent and monitoring emission spectrofluorophotometrically. Suitable labeled agents include labeled IgG, IgM, and IgA. Procedures for making and using labeled agents to determine the quantity of antibody, binding portion thereof, or probe are well known to those skilled in the art. The relationship between the quantity of labeled agent and the quantity of antibody, binding portion thereof, or probe depends on the number of labeled agents which bind to each antibody, binding portion thereof, or probe. Typically, exactly one labeled agent, binding portion thereof, or probe binds to each antibody, binding portion thereof, or probe. Consequently, the quantity of labeled agent is typically equal to the quantity of antibody, binding portion thereof, or probe present.

The relationship between the quantity of antibody, binding portion thereof, or probe and the quantity of protein depends on the number of antibodies, binding portions thereof, or probes which bind to each protein. Usually exactly one antibody, binding portion thereof, or probe binds to each protein. Consequently, the quantity of protein typically equals the quantity of antibody, binding portion thereof, or probe.

The quantity of protein on the red blood cells can be the total quantity of protein on all of the red blood cells in the sample (i.e., the sum of the quantity of protein on each of the red blood cells, summed over all of the red blood cells in the sample). This quantity is most easily determined by measuring a property of the red blood cells collectively. For example, where the antibody, binding portion thereof, or probe is a fluorescent monoclonal antibody, the aggregate quantity of protein on all the red blood cells in the sample is determined by measuring the fluorescence of the sample in bulk.

The quantity of protein on the red blood cells can also be detected by measuring the quantity of protein on each red blood cell in the sample. One suitable method for effecting such cell-by-cell measurement employs flow cytometry techniques, such as those described by Longobardi, *Flow Cytometry: First Principles*, New York: Wiley-Liss, Inc., pp 75–101 (1992), which is hereby incorporated by reference. Briefly, the flow cytometer is equipped with a means for measuring the label employed in the labeled antibody, binding portion thereof, or probe, or in the labeled agent. Preferably the label is fluorescent or radioactive and, more preferably fluorescent. The red blood cells are pumped into a capillary tubule, the diameter of which requires that the cells pass single file through a detection region of the capillary tubule. The detection region is exposed to a light of wavelength which excites the label, and fluorescent emission is detected through a narrow band emission filter of appropriate wavelength. Compared to the bulk techniques, previously described, measuring the quantity of protein on each red blood cell individually reduces inner filter effect errors and, therefore, provides a more accurate estimate the quantity of protein on the red blood cells in the sample and a more accurate determination of prior radiation exposure. A second, and perhaps more important reason for preferring the cell-by-cell technique is that it permits enumeration of cells bearing the protein. It is believed that radiation exposure causes a mutation which causes expression of the protein on the cell. Consequently, the number of cells expressing the protein is indicative of the degree of mutation. Therefore, it is believed that the number of cells bearing the protein is a better indicator of prior exposure than the aggregate amount of protein present on a plurality of cells.

The quantity of protein on the red blood cells of the sample is then correlated to the mammal's prior exposure to radiation or radiomimetic agents. Generally, correlation is effected by determining a standard quantity of protein on the red blood cells of a mammal which had been exposed to a known amount of radiation ("standard mammal"). The relative exposures of the mammal being tested and standard mammal, is then determined by comparing the quantity of protein on the red blood cells of the test mammal to that of the standard mammal. The standard mammal should be from the same mammalian species as the test mammal being evaluated. The quantity of protein on the red blood cells of the standard mammal can be determined by the above-described procedures. The amount of radiation to which the standard mammal was exposed may be determined by controlling, from birth, the environment, and, hence, the radiation exposure, of the standard mammal. This is a particularly precise and effective method where the mammal is a rat or other non-human mammal. However, the method is impractical for humans. Another method suitable for non-human mammals involves monitoring anemic stress response of RBCp production in the mammal and correlating the reduction in response with radiation exposure in accordance with the procedures outlined by Gong et al., "A Method for Determining Residual Injury in the Hematopoietic System of the X-Irradiated Rat," *Radiation Research*, 37 (3):467–477 (1969) ("Gong (1969)"), which is hereby incorporated by reference. Another method, suitable for all mammals, including humans, is described by Gong et al., "Effects of Low-Level (1.0 R) X-Irradiation on the Erythroid Response of the Rat Bone Marrow," *Radiation Research*, 65:83–97 (1976) ("Gong (1976)"), which is hereby incorporated by reference. Briefly, the method is based on the observation that, in non-anemic subjects, RBCp count increases with increasing radiation exposure. By obtaining a bone marrow sample from an individual, determining the RBCp count, and correlating the RBCp count to the radiation level to which the individual was exposed using the dose-response relationship provided in Gong (1976), one can ascertain the amount of radiation to which the standard mammal had been exposed.

On the other hand, for human analysis, standard humans are preferably selected from a group whose radiation history is documented, for example, by film badge records from research or diagnostic laboratories, nuclear plants, or heavy metal mines. Other humans suitable for use in obtaining standard data include those subjected to radiotherapy and those exposed to radiation from nuclear accidents, such as the 1986 Chernobyl explosion and the 1979 Three Mile Island mishap.

The standard dose versus response data, thus obtained, may be used in a number of ways to correlate the quantity of protein with its corresponding radiation exposure. Suitable methods include interpolative, graphical, and mathematical methods.

Where the quantity of protein on the red blood cells is detected by determining the quantity of protein on each of the red blood cells of the sample, such as, for example, by flow cytometry, as discussed above, correlating is preferably effected by the following procedures.

The quantity of red blood cells in the sample having a quantity of protein in excess of an arbitrary number is first determined. The arbitrary number is preferably between zero and a "control quantity" of proteins. As used herein "control quantity" is the quantity of protein that is normally present on the red blood cells of mammals exposed only to background levels of radiation and radiomimetic chemicals. A cell having a quantity of protein greater than the arbitrary number is termed a "marked cell" for purposes of this application. Determination of the quantity of marked cells can be carried out, for example, by comparing the quantity of transferrin receptors on each of the red blood cells of the sample, determined on a cell-by-cell basis, for example, by flow cytometry, with the arbitrary number and enumerating those cells having a quantity greater than the arbitrary number. Comparison and enumeration can be made manually, mechanically, electrically, electronically, or optically, and either simultaneously or sequentially. Where a flow cytometer is employed, the comparison and enumeration are preferably made simultaneously by the flow cytometer. For example, the gain threshold can be adjusted so that a signal (e.g., a fluorescence emission) from a cell corresponding to or less than the arbitrary number of proteins is not amplified, while a signal greater than that corresponding to the arbitrary number is amplified. Since the only information required in this procedure is the number of cells having a property (that is, the presence of a particular protein, such as transferrin receptor, in a quantity greater than the arbitrary number), this method permits the flow cytometer to record the results as a running integer sum rather than as a series of numbers, which reduces the amount of memory required. Furthermore, the speed at which the flow cytometer operates is greatly increased, because, for most cells, there is no need for the signal to stabilize and because the amount of analog-digital conversion and data storage is dramatically reduced.

The quantity of marked cells (i.e., red blood cells in the sample having a quantity of protein in excess of the arbitrary number) is then correlated to the mammal's prior exposure to radiation or radiomimetic agents.

First, a quantity of marked cells (i.e., cells having a quantity of the protein in excess of the same arbitrary number used in determining the quantity of marked cells in the test mammal) is provided, for example, by the above-described flow cytometry procedure, for one or more standard mammals exposed to a known amount of radiation or radiomimetic agents. The amount of radiation to which each standard mammal was exposed, excessive of environmental levels, can be determined by controlling the environment and the radiation exposure of the standard mammal from birth. This is a particularly precise and effective method where the mammal is a rat. However, the method is impractical for humans. Another method suitable for non-human mammals involves monitoring anemic stress (such as the severe anemia induced by phlebotomy) response of RBCp production in the mammal and correlating the reduction in response with radiation exposure in accordance with the procedures outlined in Gong (1969). Another method, suitable for all mammals, including humans, is described in Gong (1976) and is briefly described above. Preferably, the standard humans are selected from a group whose radiation history is documented, for example, by film badge records from research or diagnostic laboratories, nuclear plants, or heavy metal mines. Other humans suitable for use in obtaining standard dose-response data include those subjected to radiotherapy and those exposed to radiation from nuclear accidents, such as the 1986 Chernobyl explosion and the 1979 Three Mile Island mishap.

The standard dose data, thus obtained, may be used in a number of ways to correlate the quantity of marked cells with radiation exposure. Suitable methods include interpolative, graphical, and mathematical methods. Where the mathematical method is employed, the equation preferably has the form $y = a + b(\log x)$ for doses between about 0.1 and 150 cGy. For doses above about 150 cGy, an equation having the form $y = c + dx + fx^2$ is preferred. In these equations, y is the increase in the quantity of erythrocytes (per hundred erythrocytes) having a quantity of transferrin receptor in excess of that present in the blood of radiation-naive individuals ("marked cells"), x is the dose, and a, b, c, d, and f are constants which can be determined empirically. As one skilled in the art will note, only four standard experiments (i.e., experiments using standard mammals) need be performed in order to precisely define the mathematical expression describing prior exposure as a function of quantity of marked cells for a particular mammal. In establishing the values of the constants in the aforementioned mathematical relationship, any acceptable statistical methodology, such as least squares analysis, may be used. Where the mammal is rat or human and the protein is transferrin receptor, the constants, a, b, c, d, and f, of the equation relating x to y are, preferably, 3.56, 2.31, 8.54, −0.00327, and 0.0000378, respectively.

Where a tabular method is used to correlate the quantity of marked cells of a rat with its corresponding radiation exposure, the data presented in Table 2 may be employed. Alternatively, the correlation may be effected using the graph presented in FIG. 2.

TABLE 2

| Increase in Quantity of Marked Cells (per 100 cells) | Prior Exposure (cGy) |
|---|---|
| 19.36 | 600 |
| 14.81 | 450 |
| 10.87 | 300 |
| 8.51 | 70 |
| 4.75 | 5.7 |
| 2.02 | 0.1 |
| 0.00 | 0.0 |

These data were obtained from and correlate to quantities of marked cells 7 weeks post-exposure. As detailed below, the quantity of marked cells decreases with time from the exposure with a half-time of about 30 weeks for rats. Consequently, to accurately determine the total dose at any time other than at 7 weeks, one would need to perform the appropriate transformation using the appropriate half-time for the mammal. However, if one's interest lies in knowing the present state of hematopoietic health, a better indicator would be the present level of unrepaired transferrin reception expression, which one could obtain using these data without transformation.

Figure 3:
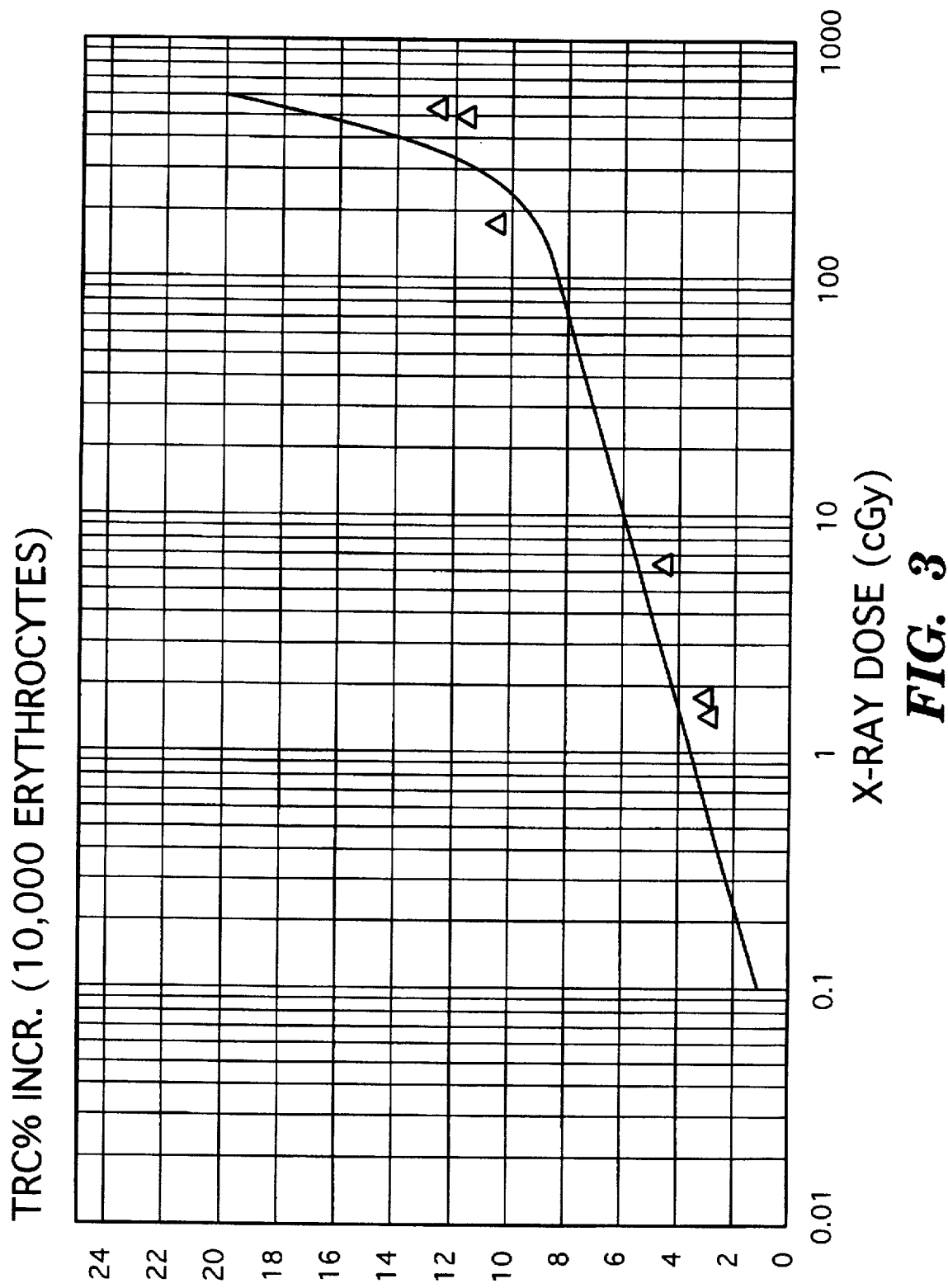
FIG. 3 is a graph of the increase in the quantity of marked cells in humans as a function of x-ray dose. The line represents the mathematical expression given in the description of FIG. 2.

To detect a human's prior exposure to radiation or radiomimetic agents, the quantity of transferrin receptor on the red blood cells, detected, for example, as described herein, can be correlated to prior radiation or radiomimetic agents exposure using the tabular method and the data presented in Table 3. The correlation can also be effected using the graph presented in FIG. 3.

TABLE 3

| Quantity of Marked Cells (per 10,000 cells) | Prior Exposure (cGy) |
|---|---|
| 1260 | 530 |
| 1160 | 489 |
| 1050 | 170 |
| 440 | 6.4 |
| 300 | 1.7 |
| 280 | 1.4 |
| 136 | 0.0 |

The mechanism which causes increased levels of transferrin receptors on mature red blood cells in mammals exposed to radiation or radiomimetic chemicals, as stated above and as shown in the examples below, has not been elucidated. However, in view of and as described in the following discussion, which is not intended to be binding or otherwise limit the scope of the present invention, the mechanism can be elucidated by those skilled in the art.

Transferrin receptor ("TR") is found on the cell surface of many types of cells (Testa et al., Crit. Rev. Oncog., 4:241–276 (1993) ("Testa"), which is hereby incorporated by reference). It is a transmembrane homodimeric glycoprotein with a molecular mass of approximately 180 kDa (Witt et al., Biochemistry, 17:3913–3917 (1978), which is hereby incorporated by reference). It functions to deliver iron into cells via an endocytic pathway of iron-transferrin complexes. Iron is required by all cells for DNA synthesis, for electron-transport reactions, and, in erythroid cells, for the synthesis of hemoglobin. Recent studies indicate that TR may have other functions as well, such as transporting viruses into cells (Cotter et al., Proc Natl. Acad. Sci., 87:4033–4037 (1990) and Franco et al., J. Exp. Med., 175:1195–1205 (1992), which are hereby incorporated by reference).

Normally, receptors are selectively concentrated in coated pits on the cell surface, and are constitutively internalized upon binding transferrin, and then recycled back to the cell surface (Goldstein et al., Annu. Rev. Biol., 1:1–39 (1985), which is hereby incorporated by reference). The receptor is a disulfide-linked dimer and consists of a 1) a cytoplasmic domain, 2) a transmembrane domain, and 3) an extracellular domain.

The gene encoding TR is approximately 31 kb in length and contains 19 exons. The mRNA transcript is 4.9 kb. Cloned cDNA covering the length of the mRNA comprises a 5' non-coding region of approximately 280 nucleotides, an open reading frame encoding the 760 amino acid peptide, and a very long 3' non-coding region of approximately 2500 nucleotides. The 5' non-coding region is encoded by the first exon, and most of the 3' non-coding region is encoded by a single exon (Kuhn et al., Cell, 37:95–103 (1984), which is hereby incorporated by reference).

TR gene expression is controlled by at least two distinct mechanisms. The first is a proliferation-dependent regulation which involves 5' non-coding sequences and operates, presumably, through transcriptional mechanisms. Studies have shown the 5' flanking region of the TR gene to contain a 115 bp region containing a TATA box and several GC rich regions which exhibit homology to promoter regions described in other genes (Testa, which is hereby incorporated by reference). Regulatory proteins bind to this region to control gene expression during cell proliferation (Miskimins, *J. Cell Biochem.*, 49:349–356 (1992), which is hereby incorporated by reference). In addition, Caset et al., *Nucleic Acids Res.*, 16:629–646 (1988), which is hereby incorporated by reference, has described an 11bp sequence identical to segments of other enhancers of, for example, polyoma virus. This sequence is 74–66 bp upstream from the mRNA start and is suggested to play an important role in the control of the transcriptional activity of the gene. The protein that binds to this sequence belongs to the family of proteins that recognize AP-1 or CRE-related sequences and that include the Jun, Fos, CREB, and ATF proteins (Beard, et al. *Nucleic Acids Res.*, 19:7117–7123 (1991), which is hereby incorporated by reference). Although the mechanisms responsible for high receptor expression in proliferating cells are not fully understood, regulatory mechanisms involved in TR mRNA stability have been elucidated.

The second mechanism controlling TR gene expression is an iron-dependent regulation involving sequences contained in the 3' non-coding region and operates through post-transcriptional mechanisms. An iron-responsive-element ("IRE") in the 3' non-coding region of the TR gene plays an important role in modulating gene expression through post-transcriptional mechanisms. This element interacts with cytoplasmic trans-acting factors, called IRE-binding proteins ("IRE-BP"). IREs are recognized by specific cytoplasmic proteins (IRE-BP), which, in the absence of iron, bind with the high affinity IREs of the TR mRNA, thereby preventing mRNA degradation. Consequently, when cellular iron becomes low, TR mRNA is stabilized, leading to an increase in translational activity and an increase in TR expression on the cell surface to sequester additional iron (Testa, which is hereby incorporated by reference).

The 3' non-coding region of the human TR mRNA contains two domains which form a specific secondary structure. This regulatory domain contains a prominent stem-loop having about 60 bp and five repeats of a palindromic sequence element. Deletions of more than one of these sequences or point mutations in the stem-loop completely abolishes the iron-dependent regulation of TR transcripts (Mullner et al., *Cell* 53:815–825 (1988), which is hereby incorporated by reference).

The half-lives of many mRNAs are modulated in response to exogenous stimuli, position in the cell cycle, or differentiation. Thus, when iron is abundant, the transferrin receptor mRNA displays a relatively short half-life (approximately 45 minutes) (Harford, In: Belasco and Brawerman, eds., *Control of Messenger RNA Stability*, New York:Academic Press, pp. 239–266, which is hereby incorporated by reference) compared to a relatively long half-life (greater than 3 hours) when iron is scarce (Koeller et al., *Proc. Natl. Acad. Sci. USA*, 88:7778–7792 (1991), which is hereby incorporated by reference). mRNA degradation is typically a continuous process with few, if any, intermediate RNA species observed. However, Binder et al., *Embo. J.*, 13:1969–1980 (1994), which is hereby incorporated by reference, report a truncated TR RNA species during the iron-regulated degradation of human TR RNA.

Because erythroid cells need iron for hemoglobin synthesis they are dependent upon TR expression. Expression of the TR gene is regulated developmentally during erythroid maturation and correlates with changing hemoglobin synthesis requirements (Chan, *Eur. J. Biochem.*, 220:683–692 (1994) and Horton, *Exp. Cell Res.*, 144:361–366 (1983), which are hereby incorporated by reference). Transferrin receptors are hyperexpressed in immature erythroid cells, in which expression is partly transcriptionally regulated by mechanisms that are not responsive to the amount of intracellular iron. Since differentiating erythroid cells lose their capacity to proliferate at times when the iron-requirement is at its peak, TR expression in these cells is likewise not related to their proliferative status. Rather, unique mechanisms distinct from non-erythroid cells are likely to be involved. To maximize iron intake, TR mRNA in erythroid cells, in addition to being induced transcriptionally, may also be stabilized. However, if post-transcriptional regulation were evident, the lack of response to iron would indicate that these mechanisms are different from those found in non-erythroid cells. Thus, TR expression appears to be regulated by a variety of mechanisms, which depend on the cell type and differentiation status of the cell (Chan, which is hereby incorporated by reference). Evidence exists suggesting that the TR genes expressed in erythroid cells may exhibit some differences when compared with those of other types of cells (Lebman et al., *Blood*, 59:671–678 (1982), which is hereby incorporated by reference). In addition, Cotner et al., *Blood*, 73:214–221 (1989), which is hereby incorporated by reference, report that erythroid cells synthesize two forms of transferrin receptor and suggest that this phenomenon may be attributed to differential mRNA splicing or to post-transcriptional modifications.

During normal physiologic pathways, in the latter part of erythroid differentiation, total cellular synthetic activities decline, and mature erythrocytes are enucleated. Normally, circulating erythroid progenitor cells are essentially $TR^-$, when compared with those found in bone marrow, which are predominantly $TR^+$ (Testa, which is hereby incorporated by reference). It is not known whether the general "shut-down" of synthetic activity in mature erythrocytes involves all activity, or whether single genes or groups of genes are shut down individually, although Chan, which is hereby incorporated by reference, suggests that the latter process is more likely. However, the mechanisms involved in the hyperinduction of the subsequent suppression of TR gene expression during the course of erythroid development remain to be determined.

Regulation of gene expression can be mostly attributed to specific alteration of proteins with binding sites found within either genomic DNA or RNA transcripts. Consequently, cellular regulation of the level of expression of individual genes often depends on the ability of nucleic acid binding proteins to modulate binding activity in response to developmental and environmental signals.

As indicated above, 1–2% of circulating erythrocytes are normally found to be $TR^+$ cells. With TR hyperexpression, however, TR levels similar to those found in bone marrow erythroid progenitor cells are detected. The persistence of the receptor on the cell surface can be attributed to one of two mechanisms. In a first mechanism, the TR peptide on the mature erythrocytes is different from the normal TR peptide found on the bone marrow erythroid progenitor cells. Consequently, TR expression eludes the normal "shut-down" and regulatory pathways, and TRs remain on the cell surface. In a second mechanism, the "shut-down" of the synthetic activity of TR expression is disrupted, such that the TR is not recognized and thereby is left intact. These disruptions may be caused, for example, by mutations within the peptide encoding region of the TR gene or by changes in the DNA or RNA binding sites, or by changes in the modulating binding proteins in those genes regulating the TR gene "shut down". Methods for detecting and quantitating the aberrant transferrin receptor on the surface of cells have been described above.

Accordingly, the present invention is also directed to a method for detecting a mammal's prior exposure to radiation or radiomimetic agents. The method includes providing a sample of nucleic acids from a nucleated cell produced by a hematopoietic stem cell. The nucleic acids have a quantity of mutations which cause expression of transferrin receptor in mature erythrocytes. The quantity is detected and is then correlated to the mammal's prior exposure to radiation or radiomimetic agents.

The nucleic acids can be DNA or RNA and can be from any nucleated cell produced by the hematopoietic stem cell. Suitable sources of nucleic acids for use in the practice of the present invention include, for example, red blood cell precursors, nucleated red blood cells, white blood cells, white blood cell precursors, platelets, platelet precursors, and mixtures thereof. The mutation can be located within the peptide encoding region of the transferrin receptor gene, which includes the open reading frame and the associated 5' and 3' non-coding regions, and can be one or more point mutations, deletions, insertions, duplications, gene amplifications, translocations, or combinations thereof.

Initial screening for the presence of a mutation in the TR gene of irradiated stem cells can be effected by Southern analysis of DNA extracted from those cells to determine if unique restricted fragment length polymorphisms ("RFLPS") are generated upon digestion with restriction endonucleases and hybridization with labeled cDNA TR probes, compared with non-irradiated control stem cells. The restricted DNA can also be hybridized with cDNA or oligonucleotide probes of those genes identified as involved in the regulation of TR expression. Consistent, unique RFLPs in DNA extracted from irradiated cells can then be exploited and used as a means to routinely screen for the presence of these mutations in nucleic acids from cells produced by the stem cells.

Southern analysis will reveal relatively major sequence differences, as detectable by restriction endonuclease digestion. In the absence of observed mutations using Southern analysis, other methodologies can be exploited to detect sequence alterations. These include, for example, RNase protection assay, exon scanning, genomic subtraction, and polymerase chain reaction ("PCR") methods, such as single-strand conformational polymorphism ("SSCP") analysis, oligoligation assays, and allele-specific PCR.

Each mutation detected, irrespective of the detecting methodologies used, is then characterized and sequenced. Routine screening can be performed, for example, by signal amplification to the mutated DNA sequence, a Southern analysis-based assay, or a chemical or enzymatic DNA amplification-based assay. The nature of the mutation ultimately determines the methodology of routine screening.

Comparison and characterization of the mRNA transcripts of TR and those genes involved in the regulation of aberrant TR on mature erythrocytes with the "normal" mRNA transcripts can be performed by Northern analyses of total RNA extracted from irradiated and control stem cells. Active synthetic activity related to the expression of the aberrant TR within irradiated cells versus non-irradiated cells can be clarified using in vitro nuclear transcription assays. Depending on these results and those of the Northern analyses, the mutation directed screening assay can employ the mRNA transcripts in a Northern analysis, a reverse-transcription amplification-based assay, or a signal amplification-based assay. Analysis of mRNA or genomic DNA are not, necessarily, mutually exclusive.

The absence of sequence alterations in either genomic DNA or mRNA indicates that post-transcriptional changes may be involved. These changes can be examined by gel retardation/gel shift mobility assays of RNA-protein complexes, where the complexes contain mRNA of those genes involved in the regulation of the aberrant TR and the appropriate RNA binding proteins.

Once a functional mutation which results in the production of aberrant TR is detected, the mutated gene can be cloned into a gene expression system, using the cloning methods described in Sambrook, which is hereby incorporated by reference, so that large quantities of the aberrant protein can be produced. The protein can then be used to raise antibodies following standard techniques, such as those described above. The antibodies are then used in a simple screening assay to detect and quantify the aberrant peptide in a peripheral blood sample.

Alternatively or additionally, cytogenetic analysis of irradiated stem cells can be used to determine the physical characteristics of the chromosomes. The physical characteristics can be used to identify the causative elements, such as gene amplification, chromosomal translocation, generation of double minutes, chromosomal insertions, or deletions, involved in the persistence of transferrin receptor on mature erythrocytes.

The quantity of mutation which causes expression of transferrin receptor in mature erythrocytes is then correlated to the mammal's prior exposure to radiation or radiomimetic agents. Correlation can be effected by comparing the quantity of mutation determined in accordance with the methods of the present invention to quantities of mutations present in standard mammals exposed to known quantities of radiation or radiomimetic agents. These methods are described in detail above, with respect to correlating quantities of transferrin receptor to prior radiation exposure.

The methods of the present invention can be used to detect a mammal's prior exposure to radiation or radiomimetic agents. Radiomimetic agents are those agents which have a mutagenic effect and include physical, chemical, and biological agents. Examples of radiomimetic agents include electromagnetic fields, chromium, lead, mercury, iron, human T cell leukemia, human papilloma virus, alcohol, cigarette smoke, dioxin, benzene, mustard gas, bleomycin, hydrogen peroxide, neocarzinostatin, and those agents disclosed in Terado et al., *Radiat. Res.* 135:189–196 (1993) and Lawley, *IARC,* 125:3–22 (1994), which are hereby incorporated by reference. Although the methods of the present invention cannot differentiate between prior exposures to radiation and radiomimetic agents, the methods are useful in detecting the aggregate exposure of the mammal to radiation and agents which have mutagenic effects indistinguishable from radiation.

The present invention is further illustrated by the following examples.

EXAMPLES

Example 1

Materials and Methods

Adult female Sprague-Dawley rats, each weighing approximately 280 g, were used throughout and were permitted to acclimate for one to two weeks prior to use in experiments.

A Westinghouse Coronado Therapeutic machine served as the source of x-rays. It was operated at 200 Kvp, 15 mA, at a target-to-skin distance of 1-2 meters, and with a beam filtration of 2.6 mm Al. The irradiation and sham-exposures were conducted on healthy, unanesthetized rats placed in plastic cages that accommodated 6-9 subjects. The x-ray output was monitored with a Victoreen condenser-R chamber placed adjacent to the animals. The dose absorbed by the bone marrow was calculated using a constant, 1R=0.88±0.05 (mean±sem) cGy, as reported in an earlier study (Gong et al., "Effects of Low-Level (1.0 R) X-Irradiation on the Erythroid Response of the Rat Bone Marrow," Radiation Research, vol. 65:83-97 (1976), the disclosure of which is hereby incorporated by reference. Briefly, the dose was determined by inserting a pair of thermoluminescent dosimeters ("TLD"), containing $CaF_2$ (MN) powder sealed in a plastic tubule) into the femurs of a sacrificed rat, irradiating them simultaneously with TLDs in open air along with a Victoreen condenser-R chamber, and comparing the resultant readings.

Two major groups of rats were employed, one for the correlation of x-ray doses with the levels of normoblasts (red blood cell precursors ("RBCp") in the bone marrow at 7 weeks post irradiation, and the other for correlation of x-ray dose with the transferrin receptor bearing ("TR") cells, a subset of erythrocytes in the blood, at 21 weeks post irradiation. In addition, two supplemental groups of animals were administered 600 cGy, and assayed for TR cells 7 and 30 weeks later. TR cell data for rats exposed to 600 cGy and assayed at 6, 21 and 30 weeks were used to determine the rate of recovery and to establish the T-1/2 of the repair of x-ray induced hematopoietic stem cell mutation.

Example 2

Enumeration of Marrow RBCp

Figure 4:
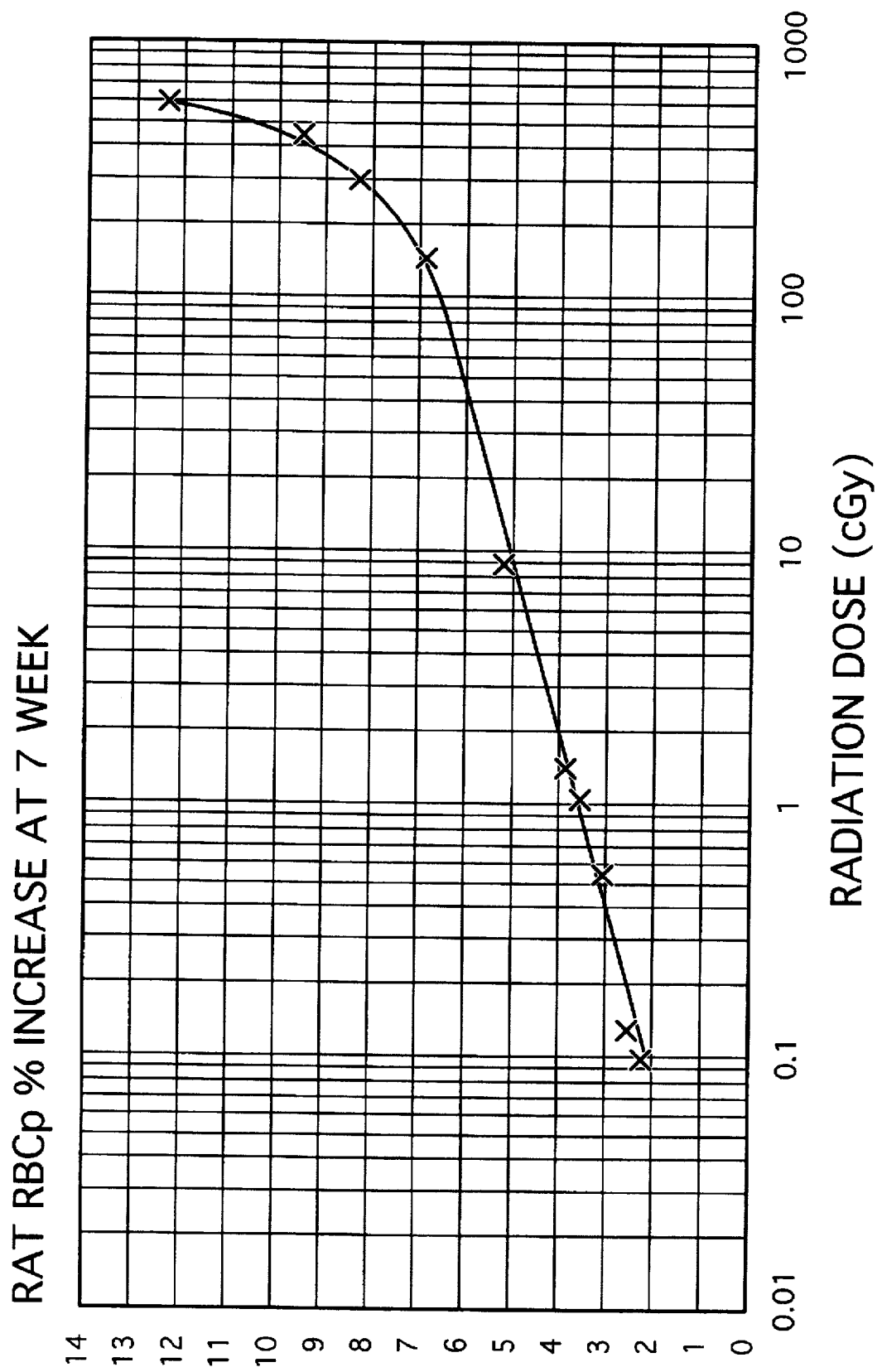
FIG. 4 is a semi-log plot of the % increase in nucleated red blood cells ("RBCp") % versus x-ray dose showing the effects of x-irradiation on nucleated RBC levels in the bone marrow. The line represents the mathematical expression: $y=a+b(\log x)$, for doses between 0.1 and 150 cGy, and $y=c+dx+fx^2$, for doses between 150 and 600 cGy, where y is the increase in the quantity of RBCp (per centium), x is the dose, and a, b, c, d, and f are 3.62, 1.44, 8.53, −0.00897, and 0.0000256, respectively.

Eleven groups of rats from two studies, one published (Gong (1983)) and one new, 10 x-ray irradiated groups (600, 450, 300, 150, 9, 1.3, 1.0, 0.5, 0.13, and 0.2 cGy) and one unexposed control group, were studied to quantify RBCp (normoblasts) in the bone marrow. At 7 weeks post-irradiation, the rats were sacrificed, the femurs were removed from the carcasses, and samples of bone marrow were obtained from the proximal epiphyses with a #2 scalpel blade. Each bone marrow sample was dispersed in a drop of serum, spread on dry, clean glass microscope slides, and stained with Wright-Giemsa stain. Samples from the eleven groups of rats were assayed by recognition and morphologic cellular enumeration under light microscopy. Five glass slides were counted per rat (approximately 1,000 hemopoietic cells each) to determine the percentage of normoblasts. For these purposes the hemopoietic nucleated marrow cells were classified as either being in an erythroid (RBCp) or non-erythroid (neutrophilic, etc.) category. The data, expressed as % nucleated RBCp of the total hemopoietic cell population, are shown in Table 4 and plotted in FIG. 4.

TABLE 4

| X-Ray Dose (cGy) | Nucleated RBC % (mean ± sd (n)) | % Increase of Nucleated RBC |
|---|---|---|
| 600[a] | 36.2 ± 0.4 (5) | 12.0 |
| 450[a] | 33.5 ± 0.4 (5) | 9.3 |
| 300[a] | 32.5 ± 0.7 (5) | 8.3 |
| 150[a] | 31.9 ± 1.3 (5) | 7.7 |
| 9[a] | 29.3 ± 0.7 (5) | 5.1 |
| Control[a] | 25.2 ± 0.5 (5) | 0.0 |

TABLE 4-continued

| X-Ray Dose (cGy) | Nucleated RBC % (mean ± sd (n)) | % Increase of Nucleated RBC |
|---|---|---|
| 1.0[b] | 27.7 ± 0.4 (50) | 3.5 |
| 0.5[b] | 27.2 ± 0.3 (65) | 3.0 |
| 0.13[b] | 26.7 ± 0.3 (75) | 2.5 |
| 0.10[b] | 26.4 ± 0.3 (85) | 2.2 |
| Control[b] | 24.2 ± 0.2 (95) | — |

[a]new data
[b]Gong (1983)

Example 3

Enumeration of Transferrin Receptors

Six groups of five rats each were irradiated with 600, 450, 300, 70, 5.7, and 0.1 cGy of x-ray radiation. A seventh group, used as a control, was treated in the same manner but not irradiated. After twenty-one weeks, five µl of blood were removed from each rat (by snipping the tail) and diluted in 1 ml of phosphate buffered saline ("PBS"). Three tubes were labeled, and 30 µl of PBS was added to each. Fifty µl of a 1:100 dilution (PBS) of anti-rat transferrin antibody and 20 µl of diluted blood were placed into tube 2. To tube 3, the control, 50 µl of a 1:100 dilution of a second antibody, IgG2a, and 20 µl of diluted blood were added. The blank tube (tube 1) contained only 100 µl of PBS. The tubes were allowed to incubate on ice for 60 minutes. Three ml of PBS were added to each tube, then mixed and centrifuged. The supernatant was carefully decanted and 500 µl of a 1:500 dilution of a fluorescein-conjugated antibody (goat anti mouse IgG+IgM.FITC) in PBS were added to tubes 2 and 3. Following 30 minutes of incubation on ice, 3 ml of PBS were added to each tube, then mixed and centrifuged. The supernatant was carefully decanted, and the pellet was resuspended in 500 µl of PBS. The samples were loaded into a Becton Dickinson FACSCAN™ flow cytometer. Using forward scatter to measure the size of the cells, and side scatter to evaluate the cell's granularity, the flow cytometer was gated to monitor only the erythrocyte population. Exciting with 490 nm radiation and gating for erythrocytes, the fluorescence of each erythrocyte was determined. 10,000 erythrocytes were sampled, and those with fluorescence greater than that of the blank (tube 3) were enumerated. The number of erythrocytes with transferrin receptor protein on their surface per 10,000 erythrocytes for each rat studied is tabulated in Table 5. The results, transformed to 7 weeks post-irradiation using the standard decay curve and a repair half-time of 30 weeks, (Example 6) and expressed as the increase in the quantity of marked cells per centum is presented in Table 2, above, and in FIG. 2.

TABLE 5

| X-Ray Dose (cGy) | 600 | 450 | 300 | 70 | 5.7 | 0.1 | Control |
|---|---|---|---|---|---|---|---|
| | 1725 | 1326 | 1103 | 946 | 592 | 465 | 330 |
| | 1511 | 1266 | 1064 | 908 | 561 | 405 | 249 |
| | 1565 | 1356 | 1005 | 931 | 756 | 420 | 378 |
| | 1797 | 1304 | 1076 | 924 | 608 | 409 | 218 |
| | 1788 | — | 968 | 801 | 625 | 480 | 340 |
| Mean | 1677 | 1313 | 1043 | 902 | 635 | 436 | 304 |
| SEM (±) | 59 | 19 | 25 | 26 | 34 | 15 | 30 |
| (N) | 5 | 4 | 5 | 5 | 5 | 5 | 5 |

Example 4

Statistical Analysis.

To establish the statistical significance of the increased levels of TR cells in the circulating blood of irradiated rats, the analysis of variance ("ANOV") was employed. The procedure provides an objective comparison of data to assess the significance of the apparent differences among the various sets of results. The analysis, summarized in Table 6 showed that the F value, the ratio of the "greater variance estimate" divided by the "lesser variance estimate," was 213 with 33 degrees of freedom. This indicates highly significant (P<0.0001) differences among the compared groups. The effects of the various doses of radiation, therefore, had a markedly significant impact on TR cellularity in the blood.

TABLE 6

| Sources of Variance | Sums of Squares | D.F. | Mean Square Variance of Estimates |
|---|---|---|---|
| Between | 703.0 | 6 | 213 |
| Within | 14.9 | 27 | 0.552 |
| Total | 717.9 | 33 | |

To assess further and to document more rigorously that all 21 of the possible radiation dose pairs (zero through 600 cGy) yielded significant differences in the levels of TR cell percentage, Duncan's Multiple Range Test was applied to the data. The results, shown in Table 7, demonstrate that all 21 dose pairs had significantly different TR cell percentages, (P<0.005). These analytical methods demonstrate that the quantity of circulating erythrocytes having transferrin receptors can be used as an index of ionizing radiation absorbed by the bone marrow.

TABLE 7

| cGy Mean % | (1) 0 3.0 | (2) 0.1 4.4 | (3) 5.7 6.4 | (4) 70 9.0 | (5) 300 10.4 | (6) 450 13.1 | (7) 600 16.8 | (8) Shortest Significant Ranges |
|---|---|---|---|---|---|---|---|---|
| (1) 3.0 | | 1.4 | 3.4 | 6.0 | 7.4 | 10.1 | 13.8 | $R_2 = 1.34$ |
| (2) 4.4 | | | 2.0 | 4.6 | 6.0 | 8.7 | 12.8 | $R_3 = 1.39$ |
| (3) 6.4 | | | | 3.6 | 4.0 | 6.7 | 10.4 | $R_4 = 1.43$ |
| (4) 9.0 | | | | | 1.4 | 4.1 | 7.8 | $R_5 = 1.46$ |
| (5) 10.4 | | | | | | 2.7 | 6.4 | $R_6 = 1.48$ |
| (6) 13.1 | | | | | | | 3.7 | $R_7 = 1.50$ |

Example 5

Interrelationship Between RBCp and TR Cells

It is apparent that the responses (increases) of the RBCp and TR cells to ionizing radiation are quantitatively and qualitatively similar, if not essentially identical. Each parameter, of course, has its own mathematical basis and numerical range of values. This is not an unexpected finding as it is well recognized that the RBCp is a direct descendent of the hematopoietic stem cells ("HSC"), and is also the immediate precursor of the circulating erythrocyte, with the TR cells representing a specific subset of the red blood cell population. Since the initial target of the radiation insult is the HSC (see Example 6, below), these findings clearly indicate that the extent of the mutagenic effects imposed upon the hematopoietic stem cells can be indexed by either the degree of RBCp elevation in the marrow or the TR cellularity enhancement in the blood. Thus, the abundance of either (marrow) red blood cell precursors (RBCp) or the (blood) TR cells could be used as a probe or index of the mutagenic status of the HSC. However, due to the ubiquity of the circulating blood, its ease of sampling, its homogeneity, and the extremely small volume required for a flow cytometry assay, the TR cellularity assay would appear to be ideal for either surveys of individuals or for massive screening of large populations. It is also possible that since many compounds and chemicals are classed as "radiomimetic" the proposed technique could be adapted for use as a scale for quantitating the degree of stem cell mutation, i.e., a measure of the mutagenic effects of the HSC expressed on a radiometric scale.

Example 6

Half-Time for Repair of Hemopoietic Stem Cell Mutation

Figure 5:
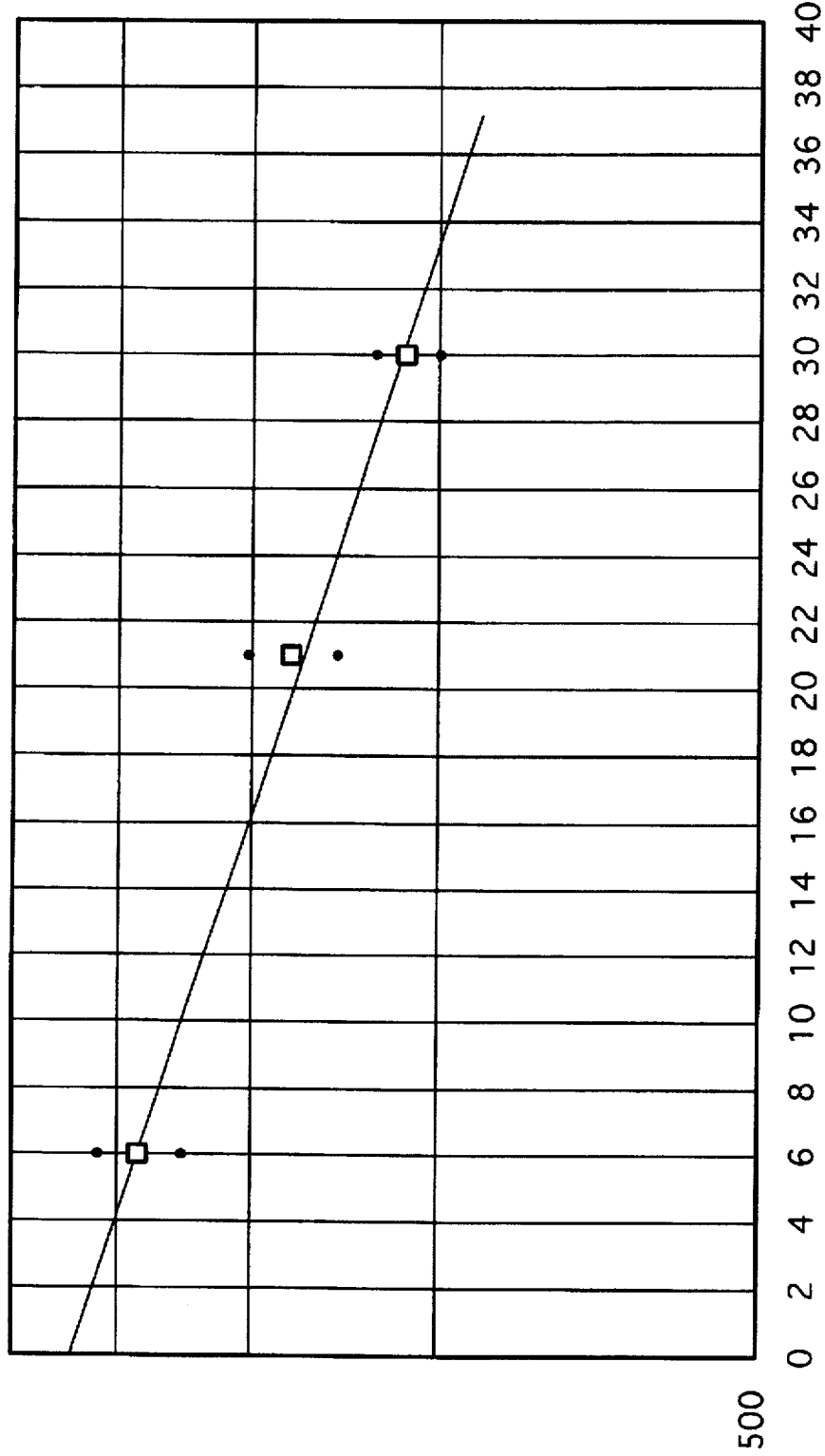
FIG. 5 is a semi-log plot of the fraction of erythrocytes having transferrin receptor thereon (◊) versus time after x-irradiation with 600 cGy in rats. The upper and lower SEM (■) are also indicated. The line represents a least square fit of the data to the standard decay curve.

The results of TR cell assays, conducted at 7, 21, and 30 weeks post exposure on five 600 cGy irradiated rats, presented in FIG. 5, reveal an exponential curve with a rate of ½ reduction of the elevated number of TR cells per 30 weeks. The X-ray-induced mutagenic alteration of the hematopoietic stem cells thus has a half-life of 30 weeks quantitated or expressed in terms of decreasing numbers (a return towards basal levels) of TR cells per 10,000 red cells in the blood. Other studies have shown similar half-lives for repair of injury caused by the X-irradiation of the hematopoietic cells in bone marrow. In Gong (1969), the disclosure of which is hereby incorporated by reference, a T-1/2 of 29 weeks was established for the suppressed normoblastic response (i.e. subnormal elevation of the RBCp in the total skeleton) following phlebotomy in the animals previously exposed to 150 cGy X-rays and tracked for 60 weeks. In Gong (1976), the disclosure of which is hereby incorporated by reference, 30 weeks was the derived T-1/2 for the expression of the lower than normal elevation of RBCp in rats exposed to 0.9 cGy X-rays and subsequently challenged by venesection and followed for 10 weeks.

Two conclusions can be drawn from these observations: (1) The similar T-1/2 values for both parameters (deficits in RBCp response in X-irradiated rats challenged by phlebotomy and increments in TR cells in irradiated but not bled subjects) implies that an assay for either could serve as a probe or window for assessing the mutational status of the hematopoietic stem cell. (2) The virtually identical T-1/2 span induced by 3 distinctively different doses of radiation (0.9, 150, and 600 cGy) indicates the rate of repair of the HSC mutations is independent of the magnitude of the X-ray dose inducing the alteration.

Example 7

Time Invariance of TR Cell Population in Humans

Blood samples were collected from five donors. All had no history of radiation exposure except for occasional dental X-rays. To test for the reproducibility and stability of an individual's level of circulating TR cells, blood samples were obtained from the volunteers initially and once again 10 days later. The results, presented in Table 8, show no significant difference in the number of cells bearing transferrin receptors ("marked cells") between the first and second assay. The mean numbers of cells bearing transferrin receptors per 10,000 circulating erythrocytes were (mean ±SD) 1390±23 and 1306±20, respectively.

TABLE 8

| Subject | Quantity of Marked Cells per 10,000 Cells First Measurement | Quantity of Marked Cells per 10,000 Cells Second Measurement |
| --- | --- | --- |
| 1 | 110 | 103 |
| 2 | 123 | 143 |
| 3 | 159 | 143 |
| 4 | 165 | 146 |
| 5 | 140 | 131 |

Example 8

Transferrin Cellularity Assays in Humans

Blood samples from six patients who were undergoing or had recently completed a radiation protocol at a Buffalo, New York hospital, none of whom had a history of hematologic malignancy or disorder, were diluted (5 μl/ml) in PBS. For each sample, 30 μl of PBS were added to each of three tubes, labeled 1, 2, and 3. 50 μl of FITC-labeled anti-human transferrin receptor antibody and 20 μl of diluted blood were placed in tube 2. To tube 3, the control, 50 μl of a 1:100 dilution of FITC-labeled IgG2a and 20 μl of diluted blood were added. Tube 1, whose volume was adjusted to 100 μl with PBS, served as a blank. The three tubes were incubated on ice for 60 minutes, and 3 ml of PBS were then added to each. After mixing, the tubes were centrifuged, the supernatant decanted, and the remaining pellet resuspended in 500 μl of PBS.

The samples were loaded into a Becton Dickinson FACSCAN™ flow cytometer gated on the erythrocyte population using forward and side scatter. Fluorescent emission of 10,000 erythrocytes, excited by 490 nm radiation, was monitored at 514 nm. Erythrocytes exhibiting fluorescence greater than that of the blank were counted. The fraction of fluorescently labeled cells indicated the fraction of cells bearing transferrin receptors on their membranes.

The fraction of cells bearing TR in each blood sample, correlated to the radiation received by its donor, is presented in Table 9 and FIG. 5. Dosages were estimated from the amount of therapeutic cobalt-60 x-ray radiation received by each donor, as indicated in the donor's treatment records. Where the radiation was directed at only a fraction of the total skeletal marrow, the fraction of the active "red" marrow at the treatment site in the field of the radiation beam was estimated. Using this estimate, the dosage was adjusted to represent whole body dosage. For example, where 5,200 cGy of radiation was used to treat a breast tumor in a patient, it was estimated that the adjacent bones which contain 10.2% of the patient's total red marrow were irradiated in the process. Consequently, the average dose to the patient's total red marrow was 530 cGy (5200 cGy×0.102). The quantity of marked cells (per 10,000 erythrocytes) in this case was 1,260 TR cells.

TABLE 9

| Quantity of Marked Cells (per 10,000 cells) | Prior Exposure (cGy) |
| --- | --- |
| 1260 | 530 |
| 1160 | 489 |
| 1050 | 170 |
| 440 | 6.4 |
| 300 | 1.7 |
| 280 | 1.4 |

Figure 6:
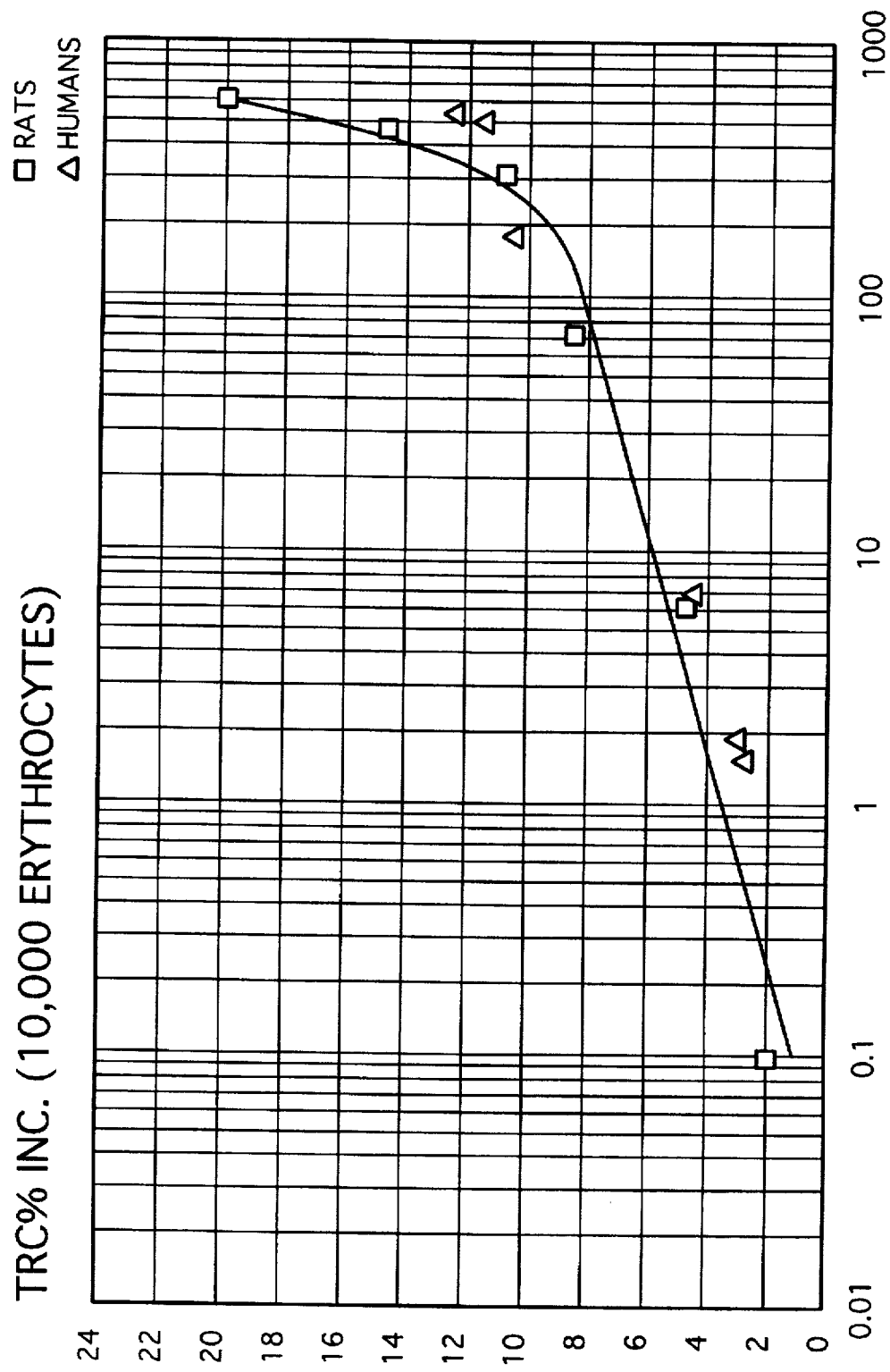
FIG. 6 is a graph of the increase in the quantity of marked cells in rats (□) and humans (Δ) as a function of x-ray dose. The line represents the mathematical expression given in the description of FIG. 2.

As the data indicate, irradiated humans demonstrate increased levels of erythrocytes bearing the transferrin receptor. Moreover, the data indicate that the dose response relationship was sufficiently sensitive over the range from 10 to 600 cGy to provide a practical measure of dose. Furthermore, the similarity of the rat and human dose response curves (which are overlaid in FIG. 6) indicates that the cellular responses to radiation are comparable.

Although the invention has been described in detail for the purpose of illustration, it is understood that such detail is solely for that purpose, and variations can be made therein by those skilled in the art without departing from the spirit and scope of the invention which is defined by the following claims.

---

What is claimed:

1. A method for detecting a mammal's prior exposure to radiation or radiomimetic agents comprising:
   providing a sample of red blood cells from a mammal, wherein the red blood cells comprise a transferrin receptor on the surface thereof whose quantity increases with increasing exposure of the mammal to radiation or radiomimetic agents beyond a baseline quantity of transferrin receptor on the surface of red blood cells that have not been exposed to radiation or radiomimetic agents;
   detecting the quantity of the transferrin receptor on the red blood cells; and
   correlating the quantity of the transferrin receptor on the red blood cells to the mammal's prior exposure to radiation or radiomimetic agents.

2. A method according to claim 1, wherein said detecting comprises:
   providing an antibody or binding portion thereof or probe recognizing the transferrin receptor;
   contacting the antibody or binding portion thereof or probe recognizing the transferrin receptor with the sample for a time sufficient to permit a quantity of the antibody or binding portion thereof or probe to bind with the transferrin receptor on the red blood cells;
   determining the quantity of the antibody or binding portion thereof or probe bound to the transferrin receptor on the red blood cells; and
   relating the quantity of the bound antibody or binding portion thereof or probe to the quantity of the transferrin receptor on the red blood cells of the sample.

3. A method according to claim 2, wherein a monoclonal antibody is used in carrying out said method, the monoclonal antibody being selected from the group consisting of a radiolabeled monoclonal antibody, a fluorescent monoclonal antibody, and mixtures thereof.

4. A method according to claim 1, wherein said detecting comprises determining the quantity of transferrin receptor on each of the red blood cells of the sample.

5. A method according to claim 4, wherein the baseline in as arbitrary number greater than or equal to a quantity of transferrin receptor on the surface of red blood cells that have not been exposed to radiation or radiomimetic agents, and wherein said correlating comprises:
   determining the quantity of red blood cells in the sample having a quantity of the transferrin receptors in excess of the arbitrary number; and
   correlating the quantity of red blood cells in the sample having a quantity of the transferrin receptors in excess of the arbitrary number to the mammal's prior exposure to radiation or radiomimetic agents.

6. A method for detecting a mammal's prior exposure to radiation or radiomimetic agents comprising:
   providing a sample of red blood cells from a mammal, wherein the red blood cells have a quantity of a transferrin receptor on the surface thereof encoded by a nucleotide sequence within a DNA locus, which locus contains a gene encoding the transferrin receptor wherein the quantity of transferrin receptor is in excess of an arbitrary baseline;
   detecting the quantity of said protein on the red blood cells of the sample; and
   correlating the quantity of the protein on the red blood cells to the mammal's prior exposure to radiation or radiomimetic agents.

7. A method according to claim 6, wherein said detecting comprises:
   providing an antibody or binding portion thereof or probe recognizing the transferrin receptor;
   contacting the antibody or binding portion thereof or probe recognizing the transferrin receptor with the sample for a time sufficient to permit a quantity of the antibody or binding portion thereof or probe to bind with the transferrin receptor on the red blood cells;
   determining the quantity of the antibody or binding portion thereof or probe bound to the transferrin receptor on the red blood cells; and relating the quantity of bound antibody or binding portion thereof or probe to the quantity of transferrin receptor on the red blood cells of the sample.

8. A method according to claim 7, wherein a monoclonal antibody is used in carrying out said method, the monoclonal antibody being selected from the group consisting of a radiolabeled monoclonal antibody, a fluorescent monoclonal antibody, and mixtures thereof.

9. A method according to claim 6, wherein said detecting comprises determining the quantity of the transferrin receptor on each of the red blood cells of the sample.

10. A method according to claim 9, wherein said correlating comprises:
   determining the quantity of red blood cells in the sample having a quantity of the transferrin receptors in excess of the arbitrary number wherein the arbitrary number is greater than or equal to a quantity of transferrin receptor on the surface of red blood cells that have not been exposed to radiation or radiomimetic agents; and
   correlating the quantity of red blood cells in the sample having a quantity of the transferrin receptors in excess of the arbitrary number to the mammal's prior exposure to radiation or radiomimetic agents.

11. A method for detecting a mammal's prior exposure to radiation or radiomimetic agents comprising:
   providing a sample of red blood cells from a mammal, wherein the red blood cells have a quantity of transferrin receptors on the surface thereof in excess of an arbitrary baseline;
   detecting the quantity of transferrin receptors on the red blood cells; and
   correlating the quantity of transferrin receptors on the red blood cells to the mammal's prior exposure to radiation or radiomimetic agents.

12. A method according to claim 11, wherein said detecting comprises:
   providing an antibody or binding portion thereof or probe recognizing the transferrin receptors;
   contacting said antibody or binding portion thereof or probe recognizing the transferrin receptors with the sample for a time sufficient to permit a quantity of the antibody or binding portion thereof or probe to bind with the transferrin receptors on the red blood cells;
   determining the quantity of the antibody or binding portion thereof or probe bound to said transferrin receptors on the red blood cells; and
   relating the quantity of the bound antibody or binding portion thereof or probe to the quantity of transferrin receptors on the red blood cells of the sample.

13. A method according to claim 12, wherein an antibody is used in carrying out said method, said antibody being selected from the group consisting of a monoclonal antibody and a polyclonal antibody.

14. A method according to claim 12, wherein the antibody is a monoclonal antibody selected from the group consisting of a radiolabeled monoclonal antibody, a fluorescent monoclonal antibody, and mixtures thereof.

15. A method according to claim 13, wherein the mammal is a human and the monoclonal antibody is anti-CD71.

16. A method according to claim 12, wherein a binding portion of an antibody is used in carrying out said method, the binding portion being selected from the group consisting of an Fab fragment, and F(ab')$_2$ fragment, and an Fv fragment.

17. A method according to claim 12, wherein a probe is used in carrying out said method.

18. A method according to claim 12, wherein said determining comprises:
   adding a labeled agent, which reacts with the antibody or binding fragment thereof or probe, to the red blood cells sample containing the bound antibody or binding fragment thereof or probe under conditions effective to permit a quantity of the labeled agent to react with a quantity of the bound antibody or binding fragment thereof or probe;
   ascertaining the quantity of the labeled agent; and
   relating the quantity of the labeled agent to the quantity of the antibody or binding fragment thereof or probe bound to the transferrin receptors.

19. A method according to claim 11, wherein said detecting comprises determining the quantity of transferrin receptors on each of the red blood cells of the sample.

20. A method according to claim 19, wherein said determining the quantity of transferrin receptors on each of the red blood cells is carried out by flow cytometry.

21. A method according to claim 19, wherein said correlating comprises:
   determining the quantity of red blood cells in the sample having a quantity of transferrin receptors in excess of the arbitrary number wherein the arbitrary number is greater than or equal to a quantity of transferrin receptor on the surface of red blood cells that have not been exposed to radiation or radiomimetic agents; and
   correlating the quantity of red blood cells in the sample having a quantity of transferrin receptors in excess of the arbitrary number to said mammal's prior exposure to radiation or radiomimetic agents.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 622 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:1:

| Ile | Glu | Phe | Thr | Asp | Ile | Ile | Lys | Gln | Leu | Ser | Gln | Asn | Thr | Tyr | Thr |
|---|---|---|---|---|---|---|---|---|---|---|---|---|---|---|---|
| 1 | | | | 5 | | | | | 10 | | | | | 15 | |

-continued

| | | | | | | | | | | | | | |
|---|---|---|---|---|---|---|---|---|---|---|---|---|---|
| Pro | Arg | Glu | Ala | Gly | Ser | Gln | Lys | Asp | Glu | Asn | Leu | Ala | Tyr | Tyr | Ile |
| | | | 20 | | | | 25 | | | | | 30 | | | |
| Glu | Asn | Leu | Phe | His | Asp | Phe | Lys | Phe | Ser | Lys | Val | Trp | Arg | Asp | Glu |
| | | 35 | | | | 40 | | | | 45 | | | | | |
| His | Tyr | Val | Lys | Ile | Gln | Val | Lys | Asn | Ser | Val | Ser | Gln | Asn | Leu | Val |
| | | 50 | | | 55 | | | | | 60 | | | | | |
| Thr | Ile | Asn | Ser | Gly | Ser | Asn | Ile | Asp | Pro | Val | Glu | Ala | Pro | Glu | Gly |
| 65 | | | | | 70 | | | | 75 | | | | | | 80 |
| Tyr | Val | Ala | Phe | Ser | Lys | Ala | Gly | Glu | Val | Thr | Gly | Lys | Leu | Val | His |
| | | | | 85 | | | | | 90 | | | | | 95 | |
| Ala | Asn | Phe | Gly | Thr | Lys | Lys | Asp | Phe | Glu | Glu | Leu | Asn | Tyr | Ser | Val |
| | | | 100 | | | | | 105 | | | | 110 | | | |
| Asn | Gly | Ser | Leu | Val | Ile | Val | Arg | Ala | Gly | Lys | Ile | Thr | Phe | Ala | Glu |
| | | 115 | | | | | 120 | | | | | 125 | | | |
| Lys | Val | Ala | Asn | Ala | Gln | Ser | Phe | Asn | Ala | Ile | Gly | Val | Leu | Ile | Tyr |
| | 130 | | | | | 135 | | | | | 140 | | | | |
| Met | Asp | Arg | Asn | Thr | Phe | Pro | Val | Val | Glu | Ala | Asp | Leu | Gln | Phe | Phe |
| 145 | | | | | 150 | | | | | 155 | | | | | 160 |
| Gly | His | Ala | His | Leu | Gly | Thr | Gly | Asp | Pro | Tyr | Thr | Pro | Gly | Phe | Pro |
| | | | | 165 | | | | | 170 | | | | | 175 | |
| Ser | Phe | Asn | His | Thr | Gln | Phe | Pro | Pro | Ser | Gln | Ser | Ser | Gly | Leu | Pro |
| | | | 180 | | | | | 185 | | | | | 190 | | |
| Ser | Ile | Pro | Val | Gln | Thr | Ile | Ser | Arg | Ala | Pro | Ala | Glu | Lys | Leu | Phe |
| | | 195 | | | | | 200 | | | | | 205 | | | |
| Lys | Asn | Met | Glu | Gly | Asn | Cys | Pro | Pro | Ser | Trp | Asn | Ile | Asp | Ser | Ser |
| | 210 | | | | | 215 | | | | | 220 | | | | |
| Cys | Lys | Leu | Glu | Leu | Ser | Gln | Asn | Gln | Asn | Val | Lys | Leu | Thr | Val | Asn |
| 225 | | | | | 230 | | | | | 235 | | | | | 240 |
| Asn | Val | Leu | Lys | Glu | Thr | Arg | Ile | Leu | Asn | Ile | Phe | Gly | Val | Ile | Lys |
| | | | | 245 | | | | | 250 | | | | | 255 | |
| Gly | Tyr | Glu | Glu | Pro | Asp | Arg | Tyr | Ile | Val | Val | Gly | Ala | Gln | Arg | Asp |
| | | | | 260 | | | | 265 | | | | | 270 | | |
| Ala | Trp | Gly | Pro | Gly | Val | Ala | Lys | Ser | Ser | Val | Gly | Thr | Gly | Leu | Leu |
| | | | 275 | | | | | 280 | | | | | 285 | | |
| Leu | Lys | Leu | Ala | Gln | Val | Phe | Ser | Asp | Met | Ile | Ser | Lys | Asp | Gly | Phe |
| | | 290 | | | | | 295 | | | | | 300 | | | |
| Arg | Pro | Ser | Arg | Ser | Ile | Ile | Phe | Ala | Ser | Trp | Thr | Ala | Gly | Asp | Tyr |
| 305 | | | | | 310 | | | | | 315 | | | | | 320 |
| Gly | Ala | Val | Gly | Pro | Thr | Glu | Trp | Leu | Glu | Gly | Tyr | Leu | Ser | Ser | Leu |
| | | | | 325 | | | | | 330 | | | | | 335 | |
| His | Leu | Lys | Ala | Phe | Thr | Tyr | Ile | Asn | Leu | Asp | Lys | Val | Val | Leu | Gly |
| | | | 340 | | | | | 345 | | | | | 350 | | |
| Thr | Ser | Asn | Phe | Lys | Val | Ser | Ala | Ser | Pro | Leu | Leu | Tyr | Thr | Leu | Met |
| | | | 355 | | | | | 360 | | | | | 365 | | |
| Gly | Lys | Ile | Met | Gln | Asp | Val | Lys | His | Pro | Ile | Asp | Gly | Lys | Tyr | Leu |
| | | | 370 | | | | 375 | | | | | 380 | | | |
| Tyr | Arg | Asn | Ser | Asn | Trp | Ile | Ser | Lys | Ile | Glu | Glu | Leu | Ser | Leu | Asp |
| 385 | | | | | 390 | | | | | 395 | | | | | 400 |
| Asn | Ala | Ala | Phe | Pro | Phe | Leu | Ala | Tyr | Ser | Gly | Ile | Pro | Ala | Val | Ser |
| | | | | 405 | | | | | 410 | | | | | 415 | |
| Phe | Cys | Phe | Cys | Glu | Asp | Glu | Asp | Tyr | Pro | Tyr | Leu | Gly | Thr | Lys | Leu |
| | | | 420 | | | | | 425 | | | | | 430 | | |
| Asp | Thr | Tyr | Glu | Ile | Leu | Ile | Gln | Lys | Val | Pro | Gln | Leu | Asn | Gln | Met |
| | | 435 | | | | | 440 | | | | | 445 | | | |

```
Val  Arg  Thr  Ala  Ala  Glu  Val  Ala  Gly  Gln  Phe  Ile  Ile  Lys  Leu  Thr
     450                 455                 460

His  Asp  Ile  Glu  Leu  Thr  Leu  Asp  Tyr  Glu  Met  Tyr  Asn  Ser  Lys  Leu
465                      470                 475                           480

Leu  Ser  Phe  Met  Lys  Asp  Leu  Asn  Gln  Phe  Lys  Ala  Asp  Ile  Lys  Asp
               485                      490                      495

Met  Gly  Leu  Ser  Leu  Gln  Trp  Leu  Tyr  Ser  Ala  Arg  Gly  Asp  Tyr  Phe
               500                 505                      510

Arg  Ala  Thr  Ser  Arg  Leu  Thr  Thr  Asp  Phe  His  Asn  Ala  Glu  Lys  Thr
          515                      520                      525

Asn  Arg  Phe  Val  Met  Arg  Glu  Ile  Asn  Asp  Arg  Ile  Met  Lys  Val  Glu
     530                 535                      540

Tyr  His  Phe  Leu  Ser  Pro  Tyr  Val  Ser  Pro  Arg  Glu  Ser  Pro  Phe  Arg
545                      550                 555                           560

His  Ile  Phe  Trp  Gly  Ser  Gly  Ser  His  Thr  Leu  Ser  Ala  Leu  Val  Glu
               565                      570                      575

Asn  Leu  Arg  Leu  Arg  Gln  Lys  Asn  Ile  Thr  Ala  Phe  Asn  Glu  Thr  Leu
               580                 585                      590

Phe  Arg  Asn  Gln  Leu  Ala  Leu  Ala  Thr  Trp  Thr  Ile  Gln  Gly  Val  Ala
          595                 600                      605

Asn  Ala  Leu  Ser  Gly  Asp  Ile  Trp  Asn  Ile  Asp  Asn  Glu  Phe
          610                 615                 620
```

( 2 ) INFORMATION FOR SEQ ID NO:2:

( i ) SEQUENCE CHARACTERISTICS:
    ( A ) LENGTH: 760 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:2:

```
Met  Met  Asp  Gln  Ala  Arg  Ser  Ala  Phe  Ser  Asn  Leu  Phe  Gly  Gly  Glu
1                   5                   10                      15

Pro  Leu  Ser  Tyr  Thr  Arg  Phe  Ser  Leu  Ala  Arg  Gln  Val  Asp  Gly  Asp
               20                  25                      30

Asn  Ser  His  Val  Glu  Met  Lys  Leu  Ala  Val  Asp  Glu  Glu  Asn  Ala
          35                  40                  45

Asp  Asn  Asn  Thr  Lys  Ala  Asn  Val  Thr  Lys  Pro  Lys  Arg  Cys  Ser  Gly
     50                  55                      60

Ser  Ile  Cys  Tyr  Gly  Thr  Ile  Ala  Val  Ile  Val  Phe  Phe  Leu  Ile  Gly
65                  70                  75                            80

Phe  Met  Ile  Gly  Tyr  Leu  Gly  Tyr  Cys  Lys  Gly  Val  Glu  Pro  Lys  Thr
               85                  90                      95

Glu  Cys  Glu  Arg  Leu  Ala  Gly  Thr  Glu  Ser  Pro  Val  Arg  Glu  Glu  Pro
               100                 105                     110

Gly  Glu  Asp  Phe  Pro  Ala  Ala  Arg  Arg  Leu  Tyr  Trp  Asp  Asp  Leu  Lys
          115                 120                     125

Arg  Lys  Leu  Ser  Glu  Lys  Leu  Asp  Ser  Thr  Asp  Phe  Thr  Ser  Thr  Ile
     130                 135                     140

Lys  Leu  Leu  Asn  Glu  Asn  Ser  Tyr  Val  Pro  Arg  Glu  Ala  Gly  Ser  Gln
145                     150                     155                       160

Lys  Asp  Glu  Asn  Leu  Ala  Leu  Tyr  Val  Glu  Asn  Gln  Phe  Arg  Glu  Phe
               165                     170                     175
```

-continued

```
Lys Leu Ser Lys Val Trp Arg Asp Gln His Phe Val Lys Ile Gln Val
        180                 185                 190
Lys Asp Ser Ala Gln Asn Ser Val Ile Ile Val Asp Lys Asn Gly Arg
        195                 200                 205
Leu Val Tyr Leu Val Glu Asn Pro Gly Gly Tyr Val Ala Tyr Ser Lys
        210                 215                 220
Ala Ala Thr Val Thr Gly Lys Leu Val His Ala Asn Phe Gly Thr Lys
225                 230                 235                 240
Lys Asp Phe Glu Asp Leu Tyr Thr Pro Val Asn Gly Ser Ile Val Ile
                245                 250                 255
Val Arg Ala Gly Lys Ile Thr Phe Ala Glu Lys Val Ala Asn Ala Glu
            260                 265                 270
Ser Leu Asn Ala Ile Gly Val Leu Ile Tyr Met Asp Gln Thr Lys Phe
        275                 280                 285
Pro Ile Val Asn Ala Glu Leu Ser Phe Phe Gly His Ala His Leu Gly
        290                 295                 300
Thr Gly Asp Pro Tyr Thr Pro Gly Phe Pro Ser Phe Asn His Thr Gln
305                 310                 315                 320
Phe Pro Pro Ser Arg Ser Ser Gly Leu Pro Asn Ile Pro Val Gln Thr
                325                 330                 335
Ile Ser Arg Ala Ala Ala Glu Lys Leu Phe Gly Asn Met Glu Gly Asp
            340                 345                 350
Cys Pro Ser Asp Trp Lys Thr Asp Ser Thr Cys Arg Met Val Thr Ser
        355                 360                 365
Glu Ser Lys Asn Val Lys Leu Thr Val Ser Asn Val Leu Lys Glu Ile
    370                 375                 380
Lys Ile Leu Asn Ile Phe Gly Val Ile Lys Gly Phe Val Glu Pro Asp
385                 390                 395                 400
His Tyr Val Val Val Gly Ala Gln Arg Asp Ala Trp Gly Pro Gly Ala
                405                 410                 415
Ala Lys Ser Gly Val Gly Thr Ala Leu Leu Leu Lys Leu Ala Gln Met
            420                 425                 430
Phe Ser Asp Met Val Leu Lys Asp Gly Phe Gln Pro Ser Arg Ser Ile
        435                 440                 445
Ile Phe Ala Ser Trp Ser Ala Gly Asp Phe Gly Ser Val Gly Ala Thr
450                 455                 460
Glu Trp Leu Glu Gly Tyr Leu Ser Ser Leu His Leu Lys Ala Phe Thr
465                 470                 475                 480
Tyr Ile Asn Leu Asp Lys Ala Val Leu Gly Thr Ser Asn Phe Lys Val
                485                 490                 495
Ser Ala Ser Pro Leu Leu Tyr Thr Leu Ile Glu Lys Thr Met Gln Asn
            500                 505                 510
Val Lys His Pro Val Thr Gly Gln Phe Leu Tyr Gln Asp Ser Asn Trp
        515                 520                 525
Ala Ser Lys Val Glu Lys Leu Thr Leu Asp Asn Ala Ala Phe Pro Phe
        530                 535                 540
Leu Ala Tyr Ser Gly Ile Pro Ala Val Ser Phe Cys Phe Cys Glu Asp
545                 550                 555                 560
Thr Asp Tyr Pro Tyr Leu Gly Thr Thr Met Asp Thr Tyr Lys Glu Leu
                565                 570                 575
Ile Glu Arg Ile Pro Glu Leu Asn Lys Val Ala Arg Ala Ala Ala Glu
            580                 585                 590
Val Ala Gly Gln Phe Val Ile Lys Leu Thr His Asp Val Glu Leu Asn
        595                 600                 605
```

-continued

| | | | | | | | | | | | | | | |
|---|---|---|---|---|---|---|---|---|---|---|---|---|---|---|
| Leu | Asp 610 | Tyr | Glu | Arg | Tyr | Asn 615 | Ser | Gln | Leu | Leu | Ser 620 | Phe | Val | Arg | Asp |
| Leu 625 | Asn | Gly | Tyr | Arg | Ala 630 | Asp | Ile | Lys | Glu | Met 635 | Gly | Leu | Ser | Leu | Gln 640 |
| Trp | Leu | Tyr | Ser | Ala 645 | Arg | Gly | Asp | Phe | Phe 650 | Arg | Ala | Thr | Ser | Arg 655 | Leu |
| Thr | Thr | Asp | Phe 660 | Gly | Asn | Ala | Glu | Lys 665 | Thr | Asp | Arg | Phe | Val 670 | Met | Lys |
| Lys | Leu | Asn 675 | Asp | Arg | Val | Met | Arg 680 | Val | Glu | Tyr | His | Phe 685 | Leu | Ser | Pro |
| Tyr | Val 690 | Ser | Pro | Lys | Glu | Ser 695 | Pro | Phe | Arg | His | Val 700 | Phe | Trp | Gly | Ser |
| Gly 705 | Ser | His | Thr | Leu | Pro 710 | Ala | Leu | Leu | Glu | Asn 715 | Leu | Lys | Leu | Arg | Lys 720 |
| Gln | Asn | Asn | Gly | Ala 725 | Phe | Asn | Glu | Thr | Leu 730 | Phe | Arg | Asn | Gln | Leu 735 | Ala |
| Leu | Ala | Thr | Trp 740 | Thr | Ile | Gln | Gly | Ala 745 | Ala | Asn | Ala | Leu | Ser 750 | Gly | Asp |
| Val | Trp | Asp 755 | Ile | Asp | Asn | Glu | Phe 760 | | | | | | | | |